(12) United States Patent
Ziv et al.

(10) Patent No.: US 11,230,710 B2
(45) Date of Patent: Jan. 25, 2022

(54) COMPOUNDS AND METHODS FOR TRANS-MEMBRANE DELIVERY OF MOLECULES

(71) Applicant: Aposense LTD., Petach-Tikva (IL)

(72) Inventors: Ilan Ziv, Kfar Saba (IL); Joseph Dubrovsky, Tel Aviv (IL); Hagit Grimberg, Herzliya (IL)

(73) Assignee: Aposense Ltd, Petach Tikva (IL)

( * ) Notice: Subject to any disclaimer, the term of this patent is extended or adjusted under 35 U.S.C. 154(b) by 150 days.

(21) Appl. No.: 16/476,557

(22) PCT Filed: Jan. 9, 2018

(86) PCT No.: PCT/IL2018/050031
§ 371 (c)(1),
(2) Date: Jul. 9, 2019

(87) PCT Pub. No.: WO2018/127927
PCT Pub. Date: Jul. 12, 2018

(65) Prior Publication Data
US 2020/0392490 A1 Dec. 17, 2020

Related U.S. Application Data

(60) Provisional application No. 62/443,822, filed on Jan. 9, 2017.

(51) Int. Cl.
| | | |
|---|---|---|
| *C12N 15/113* | (2010.01) | |
| *A61K 47/54* | (2017.01) | |
| *A61K 31/713* | (2006.01) | |
| *C07J 41/00* | (2006.01) | |

(52) U.S. Cl.
CPC .......... *C12N 15/113* (2013.01); *A61K 31/713* (2013.01); *A61K 47/554* (2017.08); *C07J 41/0072* (2013.01); *C12N 2310/14* (2013.01); *C12N 2310/3515* (2013.01)

(58) Field of Classification Search
None
See application file for complete search history.

(56) References Cited

U.S. PATENT DOCUMENTS

| | | |
|---|---|---|
| 6,028,066 A | 2/2000 | Unger |
| 8,101,666 B2 | 1/2012 | Ziv et al. |
| 8,809,514 B2 | 8/2014 | Yamada et al. |
| 9,889,202 B2 | 2/2018 | Ziv |
| 2006/0167223 A1 | 7/2006 | Pucci et al. |
| 2011/0123457 A1 | 5/2011 | Yu |
| 2012/0035362 A1 | 2/2012 | Barta et al. |
| 2013/0178512 A1 | 7/2013 | Manoharan et al. |
| 2015/0141678 A1 | 5/2015 | Payne et al. |
| 2016/0106855 A1 | 4/2016 | Ziv |
| 2017/0100486 A1 | 4/2017 | Ziv |
| 2019/0008976 A1 | 1/2019 | Ziv et al. |

FOREIGN PATENT DOCUMENTS

| | | |
|---|---|---|
| CN | 101076538 | 11/2007 |
| EA | 201991661 | 12/2019 |
| FR | 2846969 | 5/2004 |
| JP | 2001/507207 | 7/2001 |
| JP | 2011/521054 | 7/2011 |
| RU | 2007134566 | 3/2009 |
| RU | 2408605 | 10/2011 |
| RU | 2703416 | 10/2019 |
| WO | WO97/40679 | 6/1997 |
| WO | WO98/50041 | 12/1998 |
| WO | WO2005/077968 | 8/2005 |
| WO | WO2006/027711 | 3/2006 |
| WO | WO 2006/027711 A2 | 3/2006 |
| WO | WO2006/086871 | 8/2006 |
| WO | WO2009/140427 | 11/2009 |
| WO | WO2009/155335 | 12/2009 |
| WO | WO2010/033247 | 3/2010 |
| WO | WO2013/181440 | 5/2013 |
| WO | WO2013/098244 | 7/2013 |
| WO | WO2013/176772 | 11/2013 |
| WO | WO2014/062697 | 4/2014 |
| WO | WO 2014/062697 A2 | 4/2014 |
| WO | WO2014/127052 | 8/2014 |
| WO | WO2015/145417 | 1/2015 |
| WO | WO2017/029664 | 2/2017 |
| WO | WO2018/127927 | 12/2018 |
| WO | WO2019/008574 | 10/2019 |

OTHER PUBLICATIONS

Cai et al. "Effective gene delivery using stimulus-responsive catiomer designed with redox-sensitive disulfide and acid-labile imine linkers" Biomacromolecules. Apr. 9, 2012;13(4):1024-34.
Alconcel et al. "FDA-approved poly(ethylene glycol)-protein conjugate drugs", Polymer Chemistry, Jun. 2011, vol. 2, No. 14, pp. 1442-1448.
Andersen, et al., "Effect of phloretin on the permeability of thin lipid membranes", Journal of General Physiology, Jun. 1, 1976, 67-6, pp. 749-771.
Belikov V.G.; Pharmaceutical Chemistry, Ch. 26, 2007, MEDpressinform, Moscow, pp. 27-29.
Bellucci, et al., "Multicomponent Synthesis of Peptide-Sugar Conjugates Incorporating Hexafluorovaline", Advanced Synthesis & Catalysis, 2010, pp. 2791-2798, 352-16.
Blazejewski, et al., "Synthesis, Characterization and Biological Evaluation of 7[alpha]-Perfluoroalkylestradiol Derivatives", Bioorganic and Medicinal Chemistry, 2003, pp. 335-345, 11-3.

(Continued)

*Primary Examiner* — Tracy Vivlemore
(74) *Attorney, Agent, or Firm* — Mark S. Cohen; Pearl Cohen Zedek Latzer Baratz LLP

(57) ABSTRACT

A system for delivery of drugs, and especially genetic drugs such as siRNA or antisense oligonucleotides (ASO) across biological membranes is provided. It comprises a trans-membrane delivery moiety, energized by the membrane internal electrical field, and a redox-sensitive disulfide moiety, designed to be reduced at the cytoplasm, thus releasing the cargo drug to exert its pharmaceutical effects at its target sites.

8 Claims, 5 Drawing Sheets

(56) References Cited

OTHER PUBLICATIONS

Figure 1A:
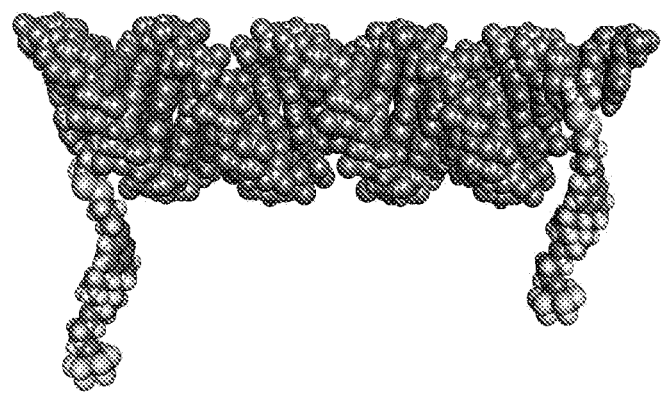

Buer et al. "Perfluoro-tert-butyl-homoserine as a sensitive 19F NMR reporter for peptide-membrane interactions in solution" Journal of Peptide Science. May 2013;19(5):308-14.
Cai, X et al. (2012). Effective gene delivery using stimulus-responsive catiomer designed with redox-sensitive disulfide and acid-labile imine linkers. Biomacromolecules, 13(4), 1024-1034.
Grijalvo, et al., "Synthesis of Oligonucleotides Carrying Amino Lipid Groups at the 3'-End for RNA Interference Studies", The Journal of Organic Chemistry, 2010, pp. 6806-6813, 75-20.
Hunt et al. "2-Arylbenzoxazoles as CETP inhibitors: Substitution and modification of the α-alkoxyamide moiety" Bioorganic & medicinal chemistry letters. Feb. 1, 2010;20(3): 1019-22.
Ikumi, et al., "Polymer-phloridzin conjugates as an anti-diabetic drug that Inhibits glucose absorption through the Na+/glucose cotransporter (SGLT1) in the small intestine", Journal of Controlled Release, Jan. 2008, 125-1, pp. 42-49.
International Search Report for Application No. PCT/IL2015/000019, dated Jul. 28, 2015.
International Search Report for PCT Application No. PCT/IL2016/50893 dated Dec. 28, 2016.
International Search Report for PCT Application No. PCT/IL2018/050031 dated May 24, 2018.
International Search Report for PCT Application No. PCT/IL2018/50714 dated Nov. 20, 2018.
Janout, et al., "Molecular Umbrella Conjugate for the Ocular Delivery of siRNA", Bioconjugate Chemistry, Jan. 16, 2014, pp. 197-201, 25-2.
Jiang et al. "The synthesis of a geminally perfluoro-tert-butylated β-amino acid and its protected forms as a potential pharmacokinetic modulator and reporter for peptide-based pharmaceuticals" The Journal of organic chemistry. Feb. 16, 2007;72(4):1464-7.
Jiang, et al., "The Design and Synthesis of Highly Branched and Spherically Symmetric Fluorinated Macrocyclic Chelators", Synthesis, 2008, pp. 215-220, vol. 2008-2.
Krafft; "Fluorocarbons and fluorinated amphiphiles in drug delivery and biomedical research" Advanced Drug Delivery Reviews, Apr. 25, 2001, vol. 47, No. 2-3, pp. 209-228.
Riess "Fluorous micro- and nanophases with a biomedical perspective" Tetrahedron, May 2002, vol. 58, No. 20, pp. 4113-4131.
Schiller, et al., "DSC measurements on full thickness mice skin: An additional tool to investigate permeation enhancement of highly lipophilic drugs", Journal of Thermal Analysis and Calorimetry, 2004, pp. 497-510, 77-2.
Seibutsu Butsuri (Biophysics) 2010, vol. 50, No. 3, pp. 137-140.
Shengguo Sun; Adejare, Adeboye; "Fluorinated Molecules as Drugs and Imaging Agents in the CNS" Current Topics in Medicinal Chemistry, Jul. 2006, vol. 6 Issue 14, pp. 1457-1464.
Shiroh Futaki, Ikuhiko Nakase; "Intracellular Delivery Using Membrane-Permeable Basic Peptides: The Molecular Mechanisms and Applications" 2010 vol. 50 Issue 3 pp. 137-140.
Üllen, etl al., "Covalent adduct formation between the plasmalogen-derived modification product 2-chlorohexadecanal and phloretin"., Biochemical Pharmacology, Feb. 15, 2015, 93-4, pp. 470-481.
Vierling et al. "Highly fluorinated amphiphiles as drug and gene carrier and delivery systems" Journal of Fluorine Chem. Feb. 2001, vol. 107 No. 2, pp. 337-354.
Wolfrum,C et al.; Mechanisms And Optimization Of In Vivo Delivery Of Lipophilic Sirnas. Nature Biotechnology, Oct. 2007; 25 (10):1149-57. doi:10.1038/nbtl339.
Yue Xuyi et al.; "Synthesis And Characterization Of Fluorinated Conjugates Of Albumin" Journal of Fluorine Chemistry. Elsevier NL (Feb. 4, 2013) vol. 152, doi: 10.1016/J.JFLUCHEM.2013.01.026, ISSN 0022-1139-p. 173-18.
Yue-Ming, D. B. L. et al. (1999). Steroid—DNA conjugates: improved triplex formation with 5-amido-(7-deoxycholic acid)-dU incorporated oligonucleotides. Bioorganic & medicinal chemistry letters, 9(13), 1789-1794.

COMPOUNDS AND METHODS FOR TRANS-MEMBRANE DELIVERY OF MOLECULES

CROSS-REFERENCE TO RELATED APPLICATIONS

This application is a National Phase Application of PCT International Application No. PCT/IL2018/050031, International Filing Date 9 Jan. 2018, claiming the benefit of U.S. Patent Application No. 62/443,822, filed 9 Jan. 2017 which is hereby incorporated by reference.

FIELD OF THE INVENTION

The invention relates to compounds, delivery system and methods for delivery of molecules and macromolecules across biological membranes into cells, destined for utilizations in vitro and in vivo; among others, in the clinical setting.

BACKGROUND

One of the major scientific advances of recent years is the completion of mapping of the human genome that yielded numerous novel targets for drug therapy. Many of these targets are intracellular, and need to be addressed by macromolecular drugs, such as genetic materials or proteins. Specifically intriguing within this realm, is the recently-discovered capability to silence the expression of specific genes by RNA interference, using small interfering RNA (siRNA). RNA interference is based on utilization of short (19-27 base pairs) double-stranded RNA sequences (designated siRNA), capable of acting, in concert with cellular biological systems [among others, the Dicer protein complex, which cleaves longer double-stranded RNA to provide siRNA; and the RNA-induced silencing complex (RISC)] to inhibit translation and mark for degradation specific mRNA sequences, thus inhibiting gene expression at the translational stage. Antisense oligonucleotide (ASO), being short sequences (usually 13-25 nucleotides) of unmodified or chemically-modified DNA molecules, complementary to a specific messenger RNA (mRNA), have also been used to inhibit expression and block production of specific disease-related target proteins. Other macromolecule drugs that aim at targeting the novel intracellular targets are protein drugs. However, albeit the tremendous potential benefits of such approaches for medical care, delivery of such macromolecules into cells remains a substantial challenge, due to the relatively large and highly-charged structures of oligonucleotides. For example, siRNA has an average molecular weight of 13 kDa, and it carries 40-50 negatively-charged phosphate groups. Indeed, trans-membrane delivery of oligonucleotides requires overcoming a very large energetic barrier. There is therefore an unmet need for novel tools for delivery of macromolecule drugs across biological membranes, both in vitro and in vivo.

SUMMARY OF THE INVENTION

The invention focuses on Conjugates and Precursors thereof, comprising macromolecule drugs, such as siRNA, linked to a novel molecular delivery system. This novel system is specifically advantageous for the delivery of genetic drugs, such as siRNA or antisense oligonucleotides, (ASO) across biological barriers, such as, phospholipid cell membranes. This novel delivery system comprises a trans-membrane delivery moiety, energized by the membrane internal electrical field, and a redox-sensitive disulfide moiety, designed to be reduced at the cytoplasm, thus releasing the cargo drug to exert its pharmaceutical effects at its target sites. It operates in both the presence or absence of plasma proteins.

In an embodiment of the invention, provided are Conjugates, having the structure as set forth in Formula (I):

Formula (I)

including pharmaceutically-acceptable salts, hydrates, solvates and metal chelates of the compound represented by the structure as set forth in Formula (I), and solvates and hydrates of the salts, wherein:

D is the drug to be delivered across biological membranes, selected from a group consisting of a small-molecule drug, a peptide, a protein, and a native or modified, single-stranded or double-stranded DNA or RNA, siRNA or ASO;

y, z and w are each an integer, independently selected from 0, 1, 2, 3, 4, 5 or 6, wherein whenever the integer is 0, it means that the respective E moiety is null; at least one of y, z or w is different from 0;

E, E', or E" can be the same or different, each having independently a structure as set forth in general Formula (II):

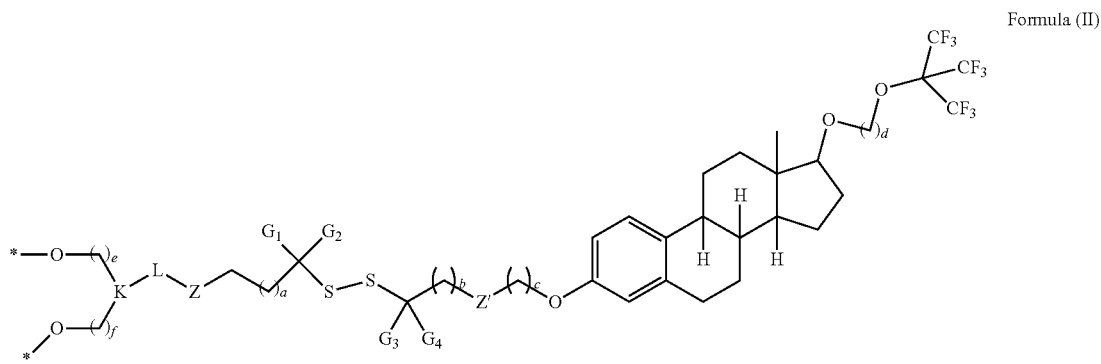

Formula (II)

including pharmaceutically acceptable salts, hydrates, solvates and metal chelates of the compound represented by the structure as set forth in Formula (II), and solvates and hydrates of the salts, wherein:

$G_1$, $G_2$, $G_3$ and $G_4$ are each independently selected from the group consisting of hydrogen, methyl or ethyl; at least two G groups are hydrogen;

Z and Z' are each independently selected from the group consisting of null; —$CH_2$—; —NH—; —N(R')—; —C(H)($CH_2$)$_n$[N(R")(R''')]—; —N($R^1$)—C(O)—C(H)($CH_2$)$_n$[N(R")(R''')]—; wherein each of R', R" and R''' is independently selected from the group, consisting of hydrogen, $C_1$, $C_2$, $C_3$, $C_4$ alkyl; or $C_1$, $C_2$, $C_3$, $C_4$ alkyl amine, wherein the amine is a primary, secondary or tertiary amine; n stands for an integer of 0, 1, 2, 3, 4; wherein n=0 means null; at least one of Z or Z' is an amine;

L is a linker, selected from null; ether; amide; ester; carbonate; carbamate group(s); one or two hydrocarbon chains, each comprising 1-4 carbon atoms, being optionally-substituted by hydroxyl or amine group(s); or any combination thereof;

K is selected from null, —CH— and —N—;

a is an integer, selected from the group consisting of 0, 1, 2, 3 and 4;

b is an integer, selected from the group consisting of 0, 1, 2, 3 and 4;

c is an integer, selected from the group consisting of 1, 2, 3 and 4;

d is an integer, selected from the group consisting of 2, 3 and 4;

e, f are each an integer, selected independently form the group consisting of 0, 1, 2 and 3;

* is selected from the group consisting of hydrogen; a linkage point to D; a linkage point to a protecting group for alcohol; a linkage point to a phosphate, sulfate or carboxyl group; and a linkage point to a solid support.

In another embodiment, there is provided a Conjugate according to Formula (I), wherein at least one of E, E' or E" has the structure as set forth in Formula (III):

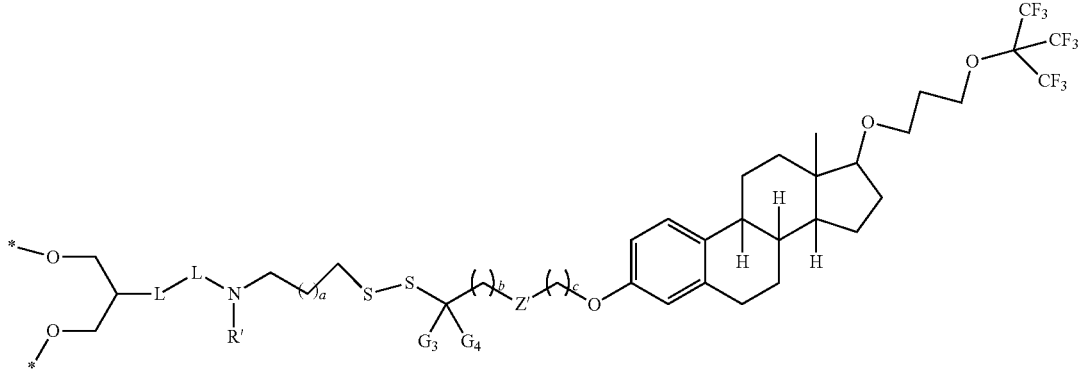

Formula (III)

including pharmaceutically acceptable salts, hydrates, solvates and metal chelates of the compound represented by the structure as set forth in Formulae (III), and solvates and hydrates of the salts, wherein Z', R', L, $G_3$, $G_4$, a, b, c and * are each as defined in Formula (II).

In another embodiment, there is provided a Conjugate according to Formula (III), wherein at least one of E, E' or E" has the structure as set forth in Formula (V):

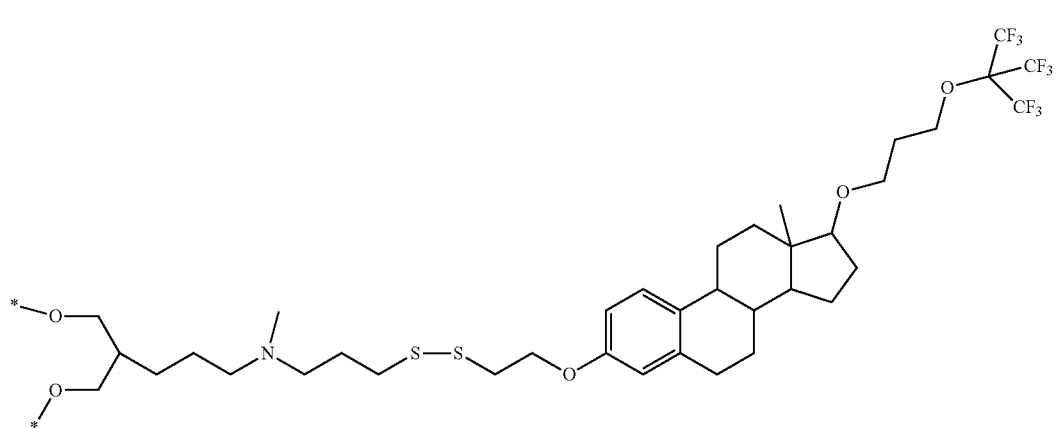

Formula (V)

including pharmaceutically acceptable salts, hydrates, solvates and metal chelates of the compound represented by the structure as set forth in Formulae (V), and solvates and hydrates of the salts.

In still another embodiment, the Invention, it provides a Conjugate according to Formula (I), wherein at least one of E, E' or E" has the structure as set forth in Formula (VI):

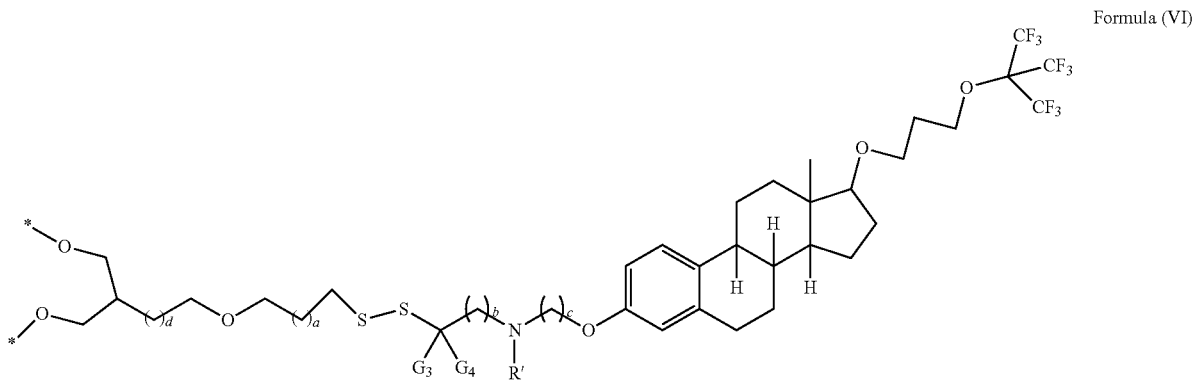

Formula (VI)

including pharmaceutically acceptable salts, hydrates, solvates and metal chelates of the compound represented by the structure as set forth in Formulae (VI), and solvates and hydrates of the salts. Wherein R', $G_3$, $G_4$, a, b, c, d and * are each as defined in Formula (II).

In a more specific embodiments, there is provided a Conjugate according to Formula (VI), wherein at least one of E, E' or E" has the structure as set forth in Formulae (VII) or (VIIa):

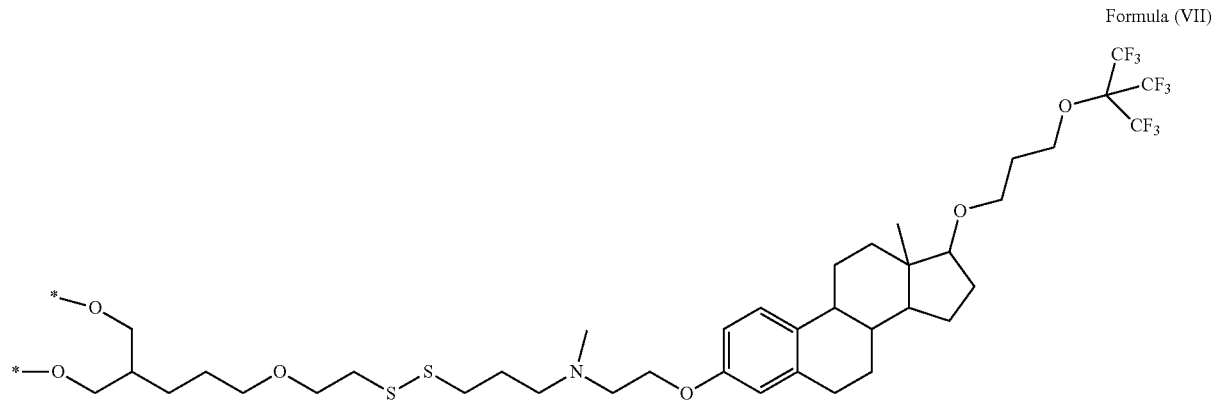

Formula (VII)

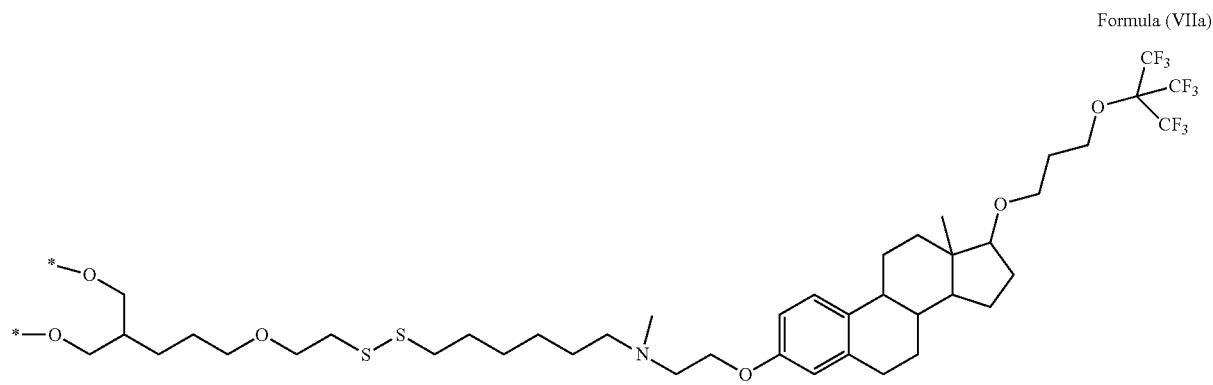

Formula (VIIa)

including pharmaceutically acceptable salts, hydrates, solvates and metal chelates of the compound represented by the structure as set forth in Formulae (VII) or (VIIa), and solvates and hydrates of the salts. An E moiety according to Formula (VII) is designated Apo-Si-K-93-A.

In another embodiment, the Invention provides a Conjugate according to Formula (II), wherein at least one of E, E' or E" has the structure as set forth in Formulae (VIII) or (VIIIa).

in need thereof. Another embodiment of the invention, relates to the use of a conjugate as described herein in the preparation of a medicament for treating a medical disorder in a patient in need thereof. In some embodiments of the invention, the medical disorder is cancer. In other embodiments, the Conjugate will have anti-infectious properties, and thus will be useful for the treatment of infectious diseases, such as bacterial or viral infections.

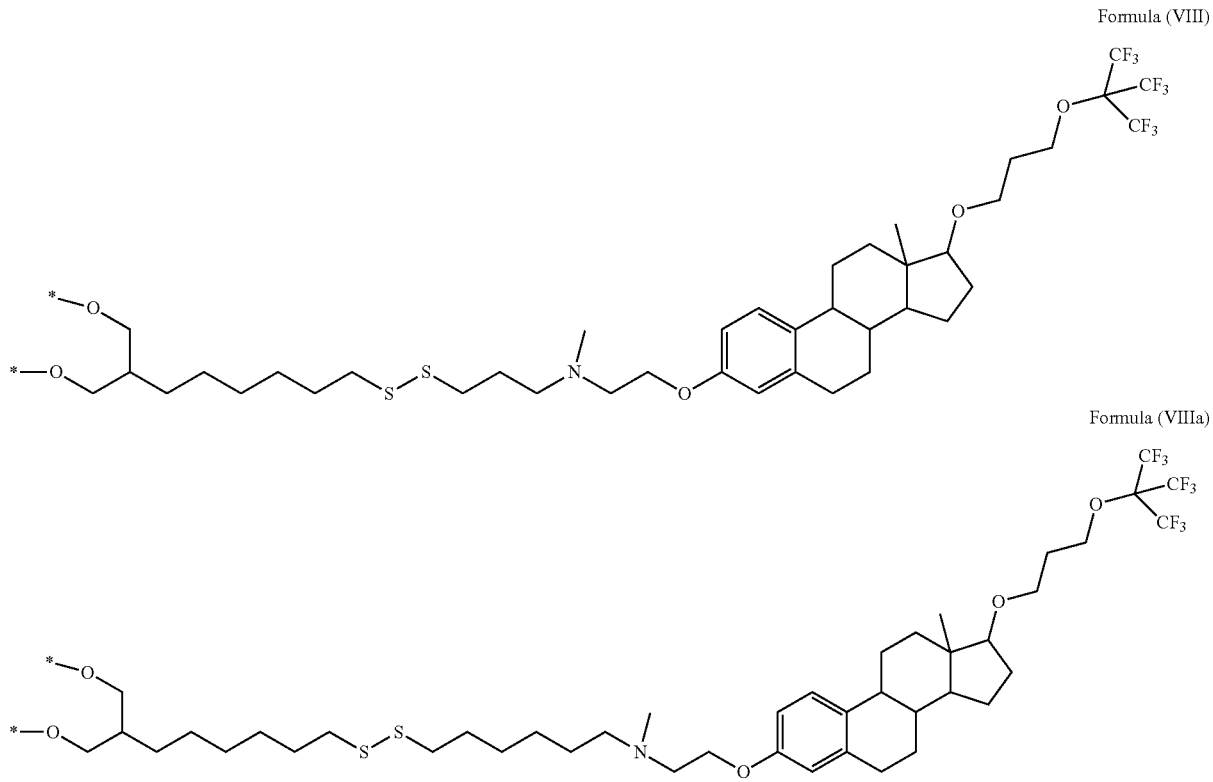

Formula (VIII)

Formula (VIIIa)

including pharmaceutically acceptable salts, hydrates, solvates and metal chelates of the compound represented by the structure as set forth in Formulae (VIII) or (VIIIa), and solvates and hydrates of the salts. An E moiety according to Formula (VIIIa) is designated Apo-Si-K-63-A.

Some embodiments of the invention relate to a method for delivery of a drug across a biological membrane into cells, either in vitro or in vivo, the method comprising contacting the cells with a Conjugate as described herein.

Another embodiment relates to a method for treating a medical disorder in a patient in need; the method comprising administration to the patient in need therapeutically-efficient amounts of a pharmaceutical composition, that comprises a Conjugate as described herein.

Another embodiment of the invention relates to a conjugate as described herein for use in medical practice; for example, in human or veterinary medicine.

Another embodiment of the invention, relates to the use of one or more of moiety E, E' or E" as set forth in Formulae (II), (III), (IV), (IVa), (V), (Va), (VI), (VII), (VIIa), (VIII) or (VIIIa) and a drug, for preparation of a Conjugate as described herein, for treating a medical disorder in a patient

BRIEF DESCRIPTION OF THE FIGURES AND DRAWINGS

Figure 1B:
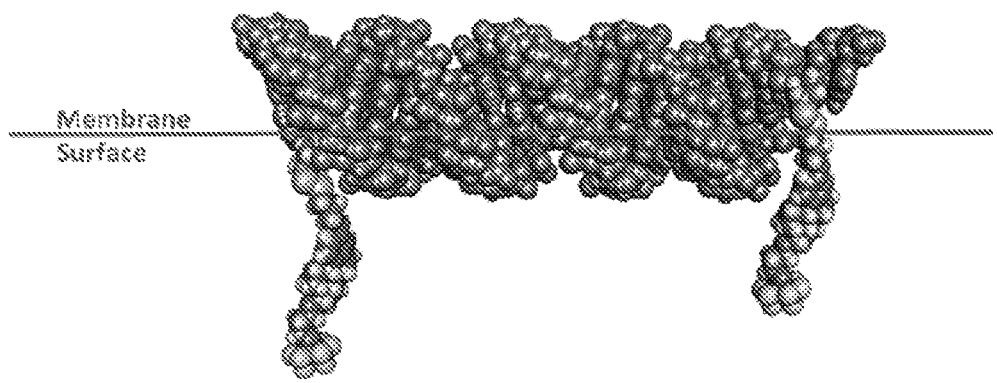
Figure 1C:
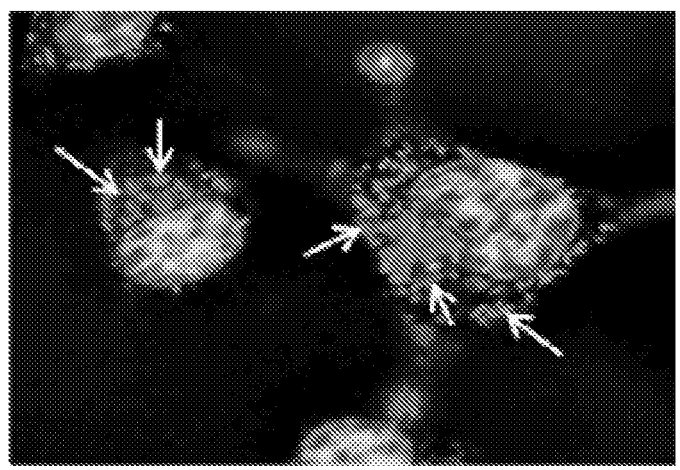

FIGS. 1a, 1b and 1c demonstrate: Figure (1a) shows a Conjugate of the Invention, comprising two E moieties, each positioned at the 5'-end of a strand of a siRNA Duplex; Figure (1b) shows the Conjugate upon its interaction with membrane, with the siRNA being parallel to the membrane surface, in a position to induce of strain and structural perturbations the outer membrane leaflet; Figure (1c) shows endocytosis, induced by the Conjugate, as a consequence of the strain and structural perturbations. The arrows exemplify endocytic vesicles.

Figure 2A:
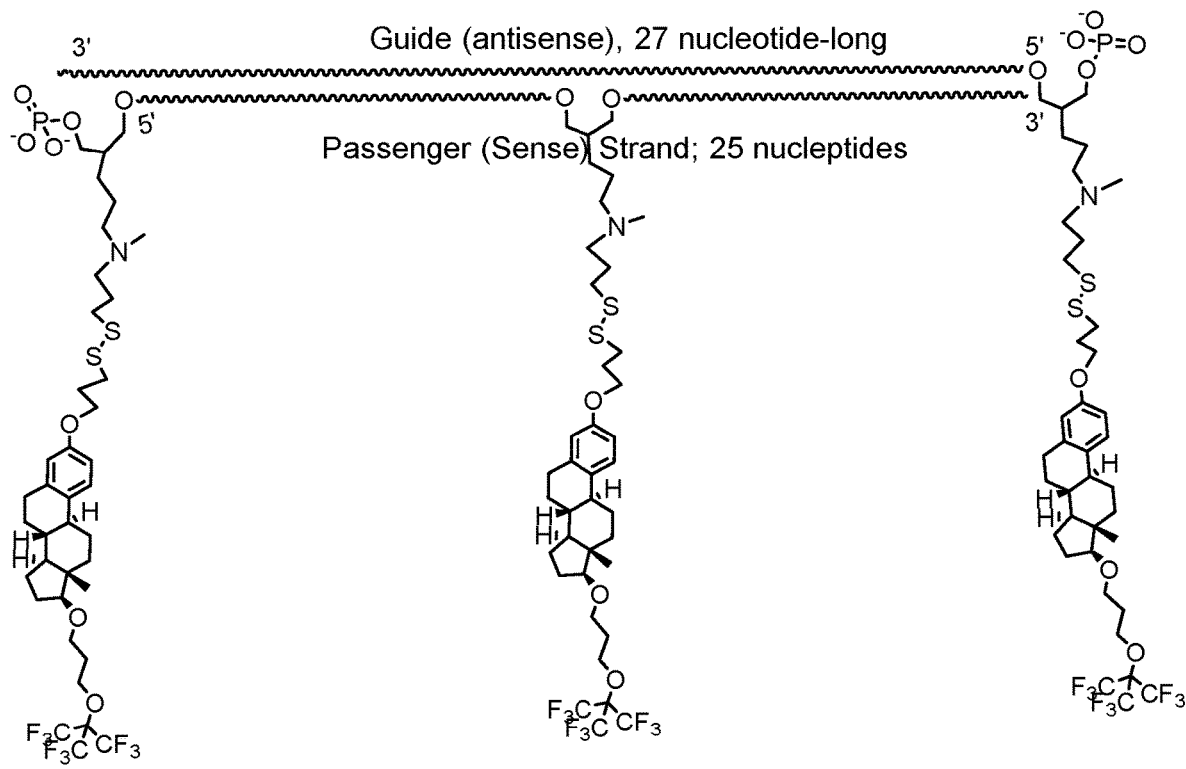
Figure 2B:
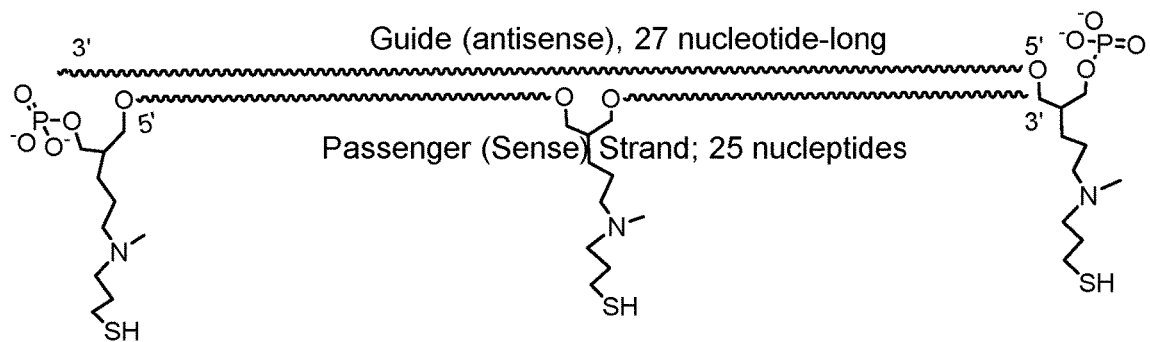
Figure 2C:
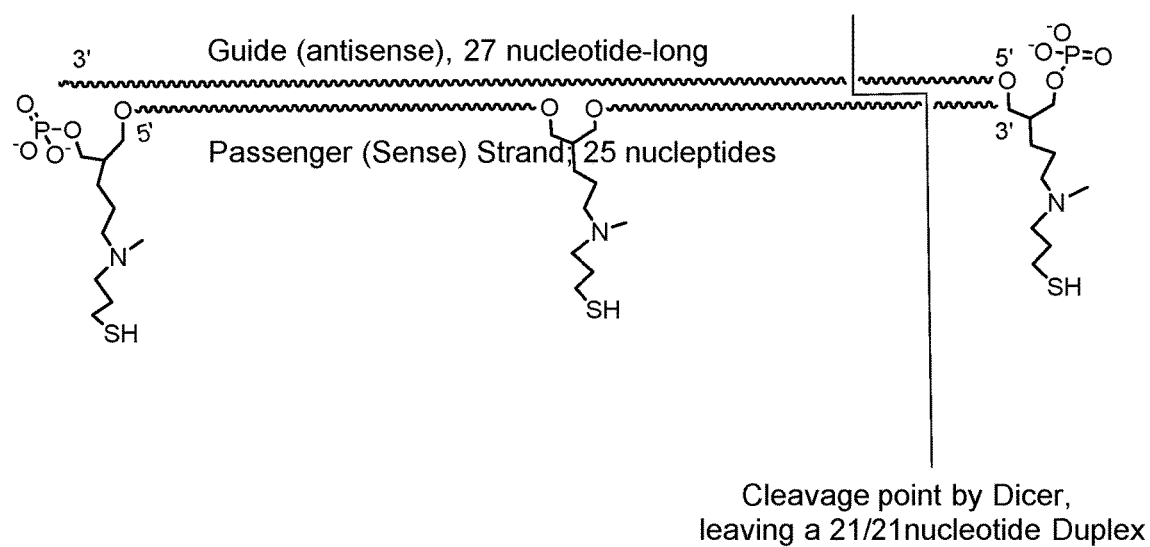
Figure 2D:
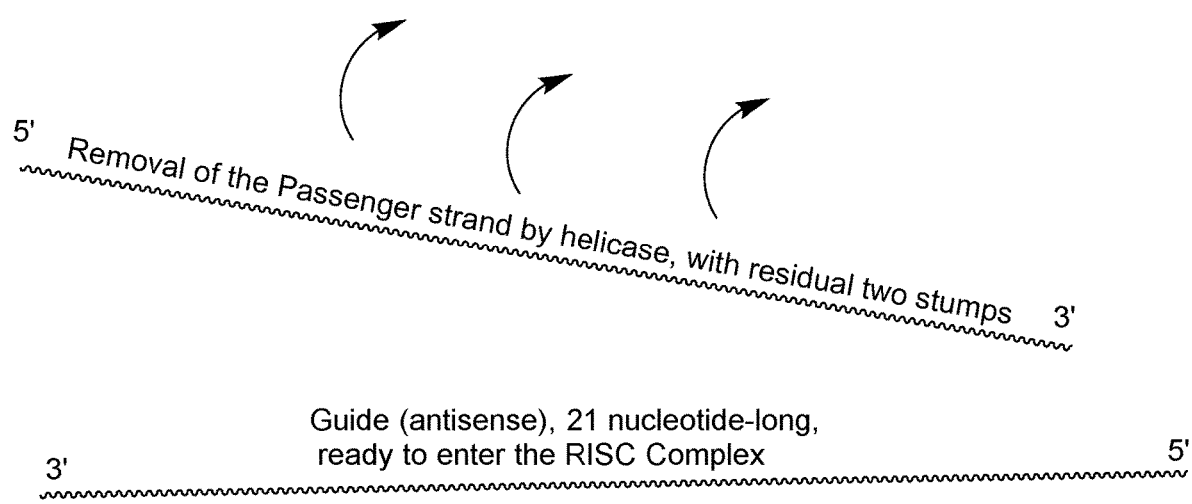

FIGS. 2a, 2b, 2c and 2d exemplify the structure of a siRNA Conjugate of the Invention, comprising three E moieties. FIG. 2a) shows the intact Conjugate at the extracellular space; FIG. 2b) demonstrates the cleavage of the E moieties, at the reductive conditions within the cytoplasm; FIG. 2c) demonstrates cleavage of the RNA Duplex, generating into a 21/23-nucleotide Duplex, thereby also removing the residual moiety of the Guide; FIG. 2d) demonstrates removal of the passenger strand by helicase with residual two stumps of the E moieties, leaving the Guide strand, ready to be delivered intact into the RISC Complex.

Figure 3:
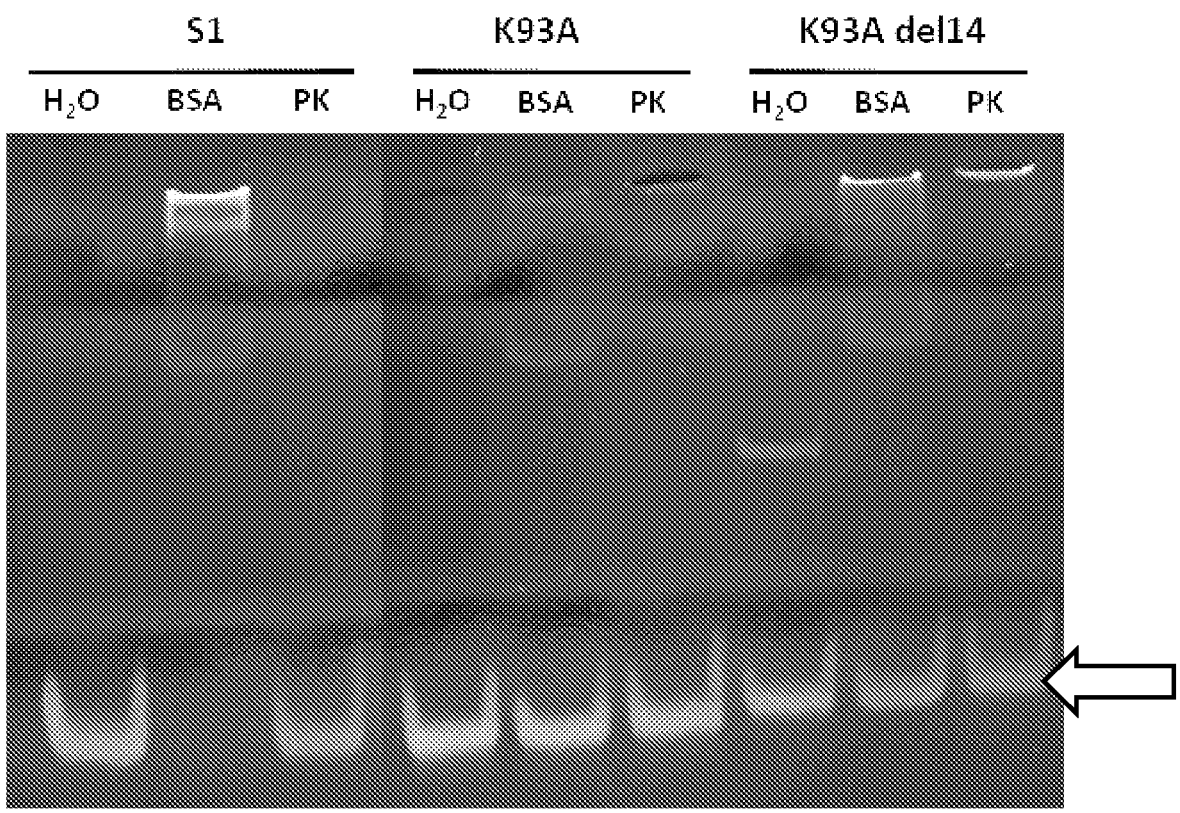

FIG. 3 demonstrates protein-bound, and protein-free fractions (Arrow), upon incubation of Conjugates of the Invention with 10% BSA. Treatment of proteinase K (PK) recovered all protein-bound Conjugates.

Figure 4:
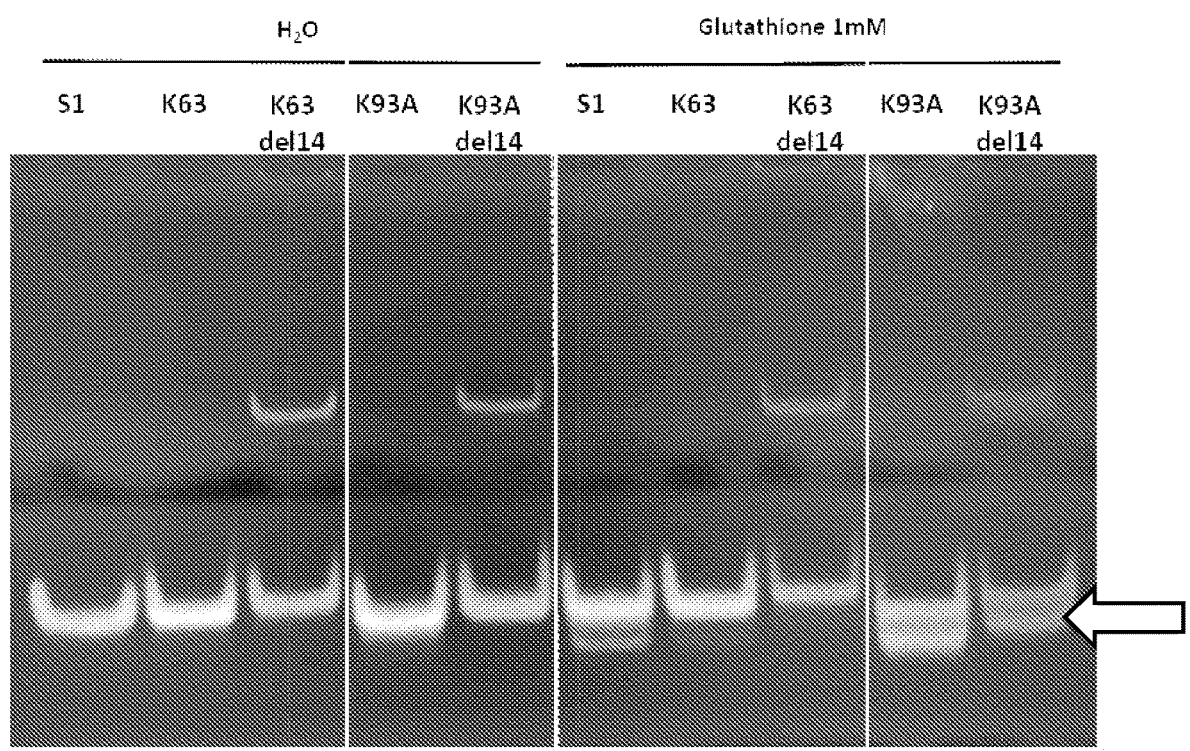

FIG. 4 demonstrates reductive cleavage of the Conjugates of the Invention (Arrow), upon incubation with reduced glutathione (1 mM for 2 hours).

DETAILED DESCRIPTION OF THE INVENTION

The invention focuses on Conjugates and Precursors thereof, comprising macromolecule drugs, such as, without being limited, oligonucleotides, which may be in some embodiments, siRNA, linked to a molecular delivery system, designed for delivery of drugs across biological membranes and biological barriers. This novel delivery system comprises a trans-membrane delivery moiety, energized by the membrane internal electrical field, and a redox-sensitive disulfide moiety, designed to be reduced at the cytoplasm, thus releasing the cargo drug to exert its pharmaceutical effects at its target sites. It operates in both the presence or absence of plasma proteins.

In an embodiment of the invention, there are provided Conjugates, having the structure as set forth in Formula (I):

Formula (I)

including pharmaceutically-acceptable salts, hydrates, solvates and metal chelates of the compound represented by the structure as set forth in Formula (I), and solvates and hydrates of the salts, wherein:

D is the drug to be delivered across biological membranes, selected from a group consisting of a small-molecule drug, a peptide, a protein, and a native or modified, single-stranded or double-stranded DNA or RNA, siRNA or ASO;

y, z and w are each an integer, independently selected from 0, 1, 2, 3, 4, 5 or 6, wherein whenever the integer is 0, it means that the respective E moiety is null; at least one of y, z or w is different from 0;

E, E', or E'' can be the same or different, each having independently a structure as set forth in general Formula (II):

including pharmaceutically acceptable salts, hydrates, solvates and metal chelates of the compound represented by the structure as set forth in Formula (II), and solvates and hydrates of the salts, wherein:

$G_1$, $G_2$, $G_3$ and $G_4$ are each independently selected from the group consisting of hydrogen, methyl or ethyl; at least two G groups are hydrogen;

Z and Z' are each independently selected from the group consisting of null; —$CH_2$—; —NH—; —N(R')—; —C(H)($CH_2$)$_n$[N(R'')(R''')]—; —N($R^1$)—C(O)—C(H)($CH_2$)$_n$[N(R'')(R''')]—; wherein each of R', R'' and R''' is independently selected from the group, consisting of hydrogen, $C_1$, $C_2$, $C_3$, $C_4$ alkyl; or $C_1$, $C_2$, $C_3$, $C_4$ alkyl amine, wherein the amine is a primary, secondary or tertiary amine; n stands for an integer of 0, 1, 2, 3, 4; wherein n=0 means null; at least one of Z or Z' is an amine;

L is a linker, selected from null; ether; amide; ester; carbonate; carbamate group(s); one or two hydrocarbon chains, each comprising 1-4 carbon atoms, being optionally-substituted by hydroxyl or amine group(s); or any combination thereof;

K is selected from null, —CH— and —N—;

a is an integer, selected from the group consisting of 0, 1, 2, 3 and 4;

b is an integer, selected from the group consisting of 0, 1, 2, 3 and 4;

c is an integer, selected from the group consisting of 1, 2, 3 and 4;

d is an integer, selected from the group consisting of 2, 3 and 4;

e, f are each an integer, selected independently form the group consisting of 0, 1, 2 and 3;

* is selected from the group consisting of hydrogen; a linkage point to D; a linkage point to a protecting group for alcohol; a linkage point to a phosphate, sulfate or carboxyl group; and a linkage point to a solid support.

In another embodiment, there is provided a Conjugate according to Formula (I), wherein at least one of E, E' or E'' has the structure as set forth in Formula (III):

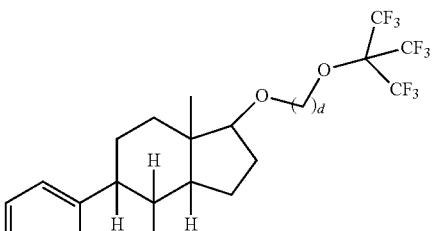

(Formula II)

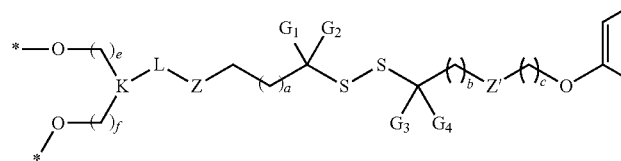

(Formula III)

including pharmaceutically acceptable salts, hydrates, solvates and metal chelates of the compound represented by the structure as set forth in Formulae (III), and solvates and hydrates of the salts, wherein Z', R', L, $G_3$, $G_4$, a, b, c and * are each as defined in Formula (II).

In another embodiment, there is provided a Conjugate according to Formula (III), wherein at least one of E, E' or E" has the structure as set forth in Formulae (IV) or (IVa):

including pharmaceutically acceptable salts, hydrates, solvates and metal chelates of the compound represented by the structure as set forth in Formulae (IV) and (IVa), and solvates and hydrates of the salts.

In another embodiment, there is provided a Conjugate according to Formula (III), wherein at least one of E, E' or E" has the structure as set forth in Formulae (V) or (Va):

(Formula IV)

(Formula IVa)

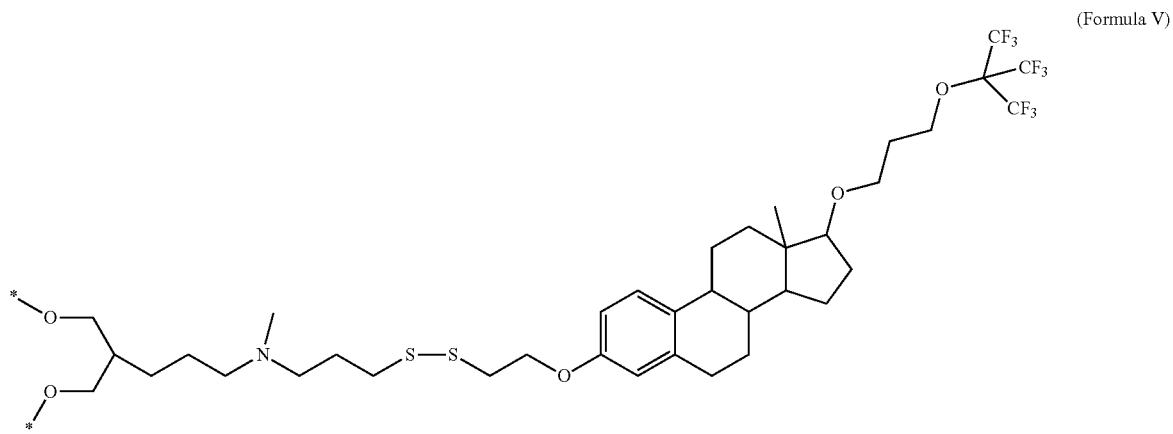 [SMILES: *OCC(CCCN(C)CCCSSCCOc1ccc2c(c1)CCC1C2CCC2(C)C(OCCCOC(C(F)(F)F)(C(F)(F)F)C(F)(F)F)CCC12)CO*]
(Formula V)

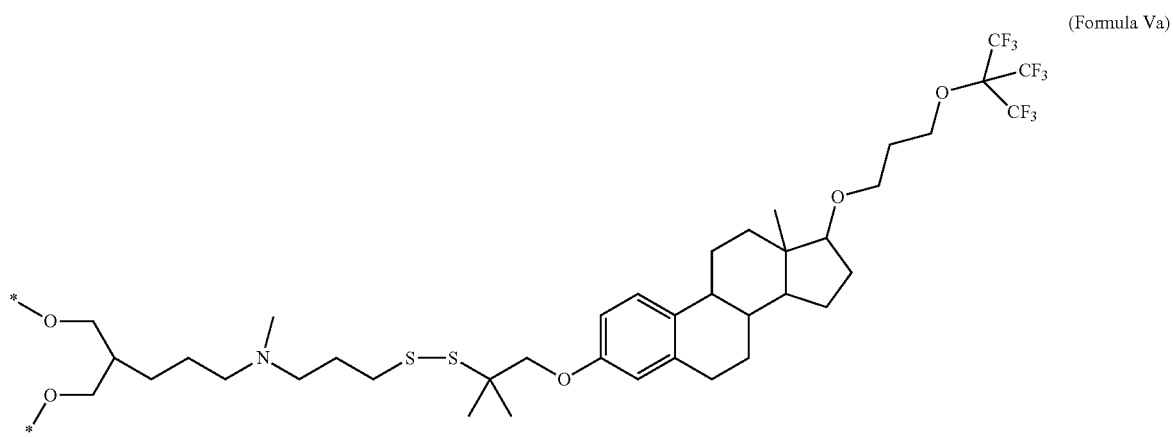
(Formula Va)

including pharmaceutically acceptable salts, hydrates, solvates and metal chelates of the compound represented by the structure as set forth in Formulae (V) or (Va), and solvates and hydrates of the salts.

In still another embodiment, the Invention, it provides a Conjugate according to Formula (I), wherein at least one of E, E' or E" has the structure as set forth in Formula (VI):

including pharmaceutically acceptable salts, hydrates, solvates and metal chelates of the compound represented by the structure as set forth in Formulae (VI), and solvates and hydrates of the salts. Wherein R', $G_3$, $G_4$, a, b, c, d and * are each as defined in Formula (II).

In a more specific embodiments, there is provided a Conjugate according to Formula (VI), wherein at least one of E, E' or E" has the structure as set forth in Formulae (VII) or (VIIa):

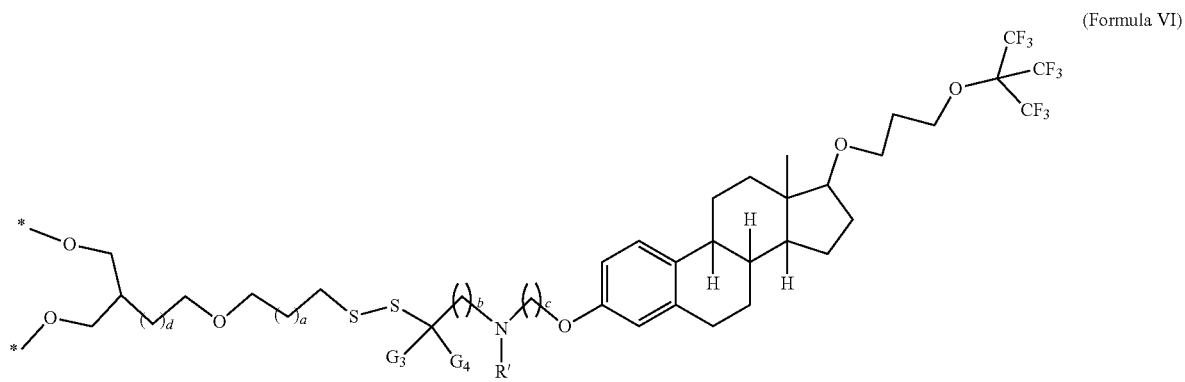
(Formula VI)

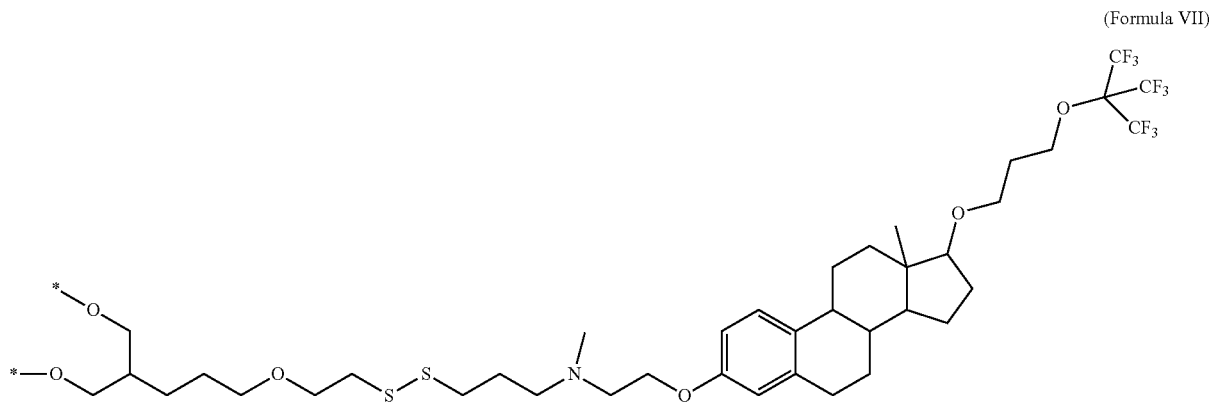

(Formula VII)

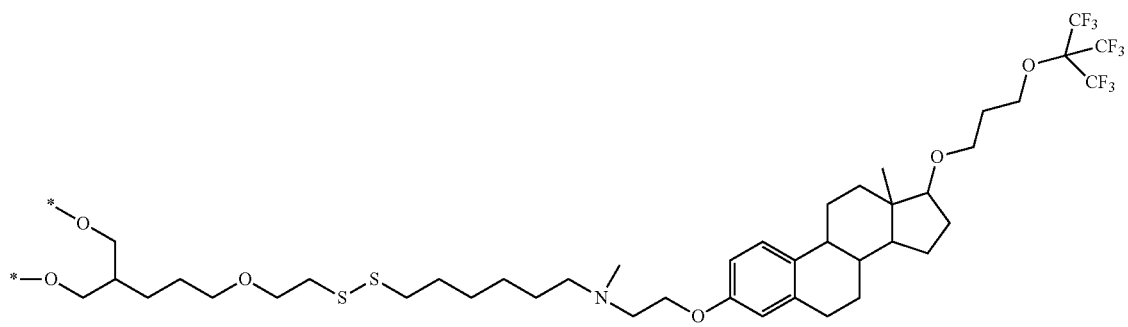

(Formula (VIIa)

including pharmaceutically acceptable salts, hydrates, solvates and metal chelates of the compound represented by the structure as set forth in Formulae (VII) or (VIIa), and solvates and hydrates of the salts. An E moiety according to Formula (VII) is designated Apo-Si-K-93-A.

In another embodiment, the Invention provides a Conjugate according to Formula (II), wherein at least one of E, E' or E" has the structure as set forth in Formulae (VIII) or (VIIIa):

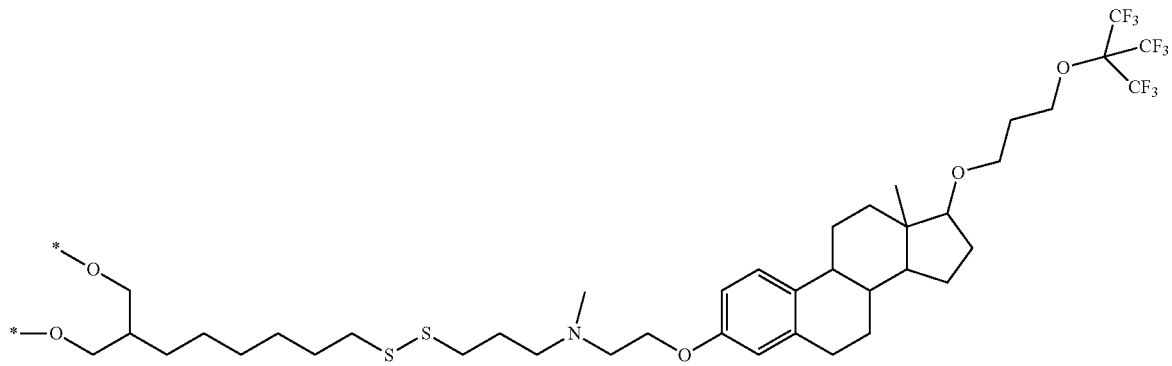

(Formula VIII)

(Formula (VIIIa))

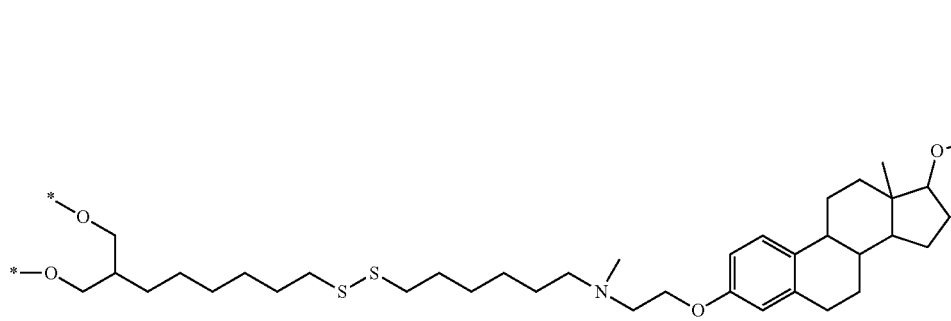

including pharmaceutically acceptable salts, hydrates, solvates and metal chelates of the compound represented by the structure as set forth in Formulae (VIII) or (VIIIa), and solvates and hydrates of the salts. An E moiety according to Formula (VIIIa) is designated Apo-Si-K-63-A.

The drugs to be delivered by the Conjugates of the Invention (i.e., moieties D) may be either small-molecule drugs or macromolecules, such as peptides, proteins or oligonucleotides (e.g., single-stranded or double-stranded, RNA or DNA). In an embodiment of the invention, the macromolecules to be delivered include RNA strands for gene silencing, i.e., siRNA (small interfering RNA), microRNA (miRNA), or DNA sequences designed to serve as antisense oligonucleotides (ASO).

Embodiments of the present invention relate to novel Conjugates, comprising a delivery system for drugs across biological membranes into the cytoplasm, or through biological barriers, such as, the blood-brain-barrier (BBB), the blood-ocular barrier (BOB), or the blood-fetal-barrier (placental-blood-barrier).

The term "protecting group for alcohol" in the context of the Invention, refers to a chemical group attached to a hydroxyl group, in order to "mask" it during certain chemical reactions, and potentially remove it thereafter, as known in the art. Examples for such protecting groups are Acetyl (Ac), Benzoyl (Bz), Benzyl (Bn), β-Methoxyethoxymethyl ether (MEM), Dimethoxytrityl, [bis-(4-methoxyphenyl)phenylmethyl] (DMT), Methoxymethyl ether (MOM), Methoxytrityl [(4-methoxyphenyl)diphenylmethyl] (MMT), p-Methoxy-benzyl ether (PMB), Pivaloyl (Piv), Tetrahydropyranyl (THP), Tetrahydrofuran (THF), Trityl (triphenylmethyl, Tr), Silyl ether [e.g., trimethylsilyl (TMS), tert-butyldimethylsilyl (TBDMS), tri-iso-propylsilyloxymethyl (TOM), and triisopropylsilyl (TIPS) ethers], Ethoxyethyl ethers (EE), phosphoramidite, N-hydroxysuccinimide (NHS).

The term "precursor" in the context of the invention, relates to an E, E' or E" of the invention, attached to chemical group(s), that is destined to be removed or modified during the synthesis of the Conjugate. Such removal or modification may occur at various stages of the synthesis; for example without limitation, during the attachment of said E, E' or E" moieties to a macromolecule drug, such as an oligonucleotide drug.

Embodiments of the invention further relate to the use of Conjugates according to the invention, comprising therapeutically-useful drugs, such as proteins or oligonucleotides (e.g., siRNA or ASO), for the treatment of medical disorders in a subject in need thereof. The medical disorders may be, without limitation, degenerative disorders, cancer, traumatic, toxic or ischemic insults, infections or immune-mediated disorders; in which specific protein(s) play(s) a role in either disease etiology or pathogenesis, and where modulation of the expression of the respective gene(s), through siRNA or antisense mechanisms, or modulation of the activity of the respective protein by a therapeutic protein such as by an antibody, or by protein replacement therapy, may have beneficial effects in inhibiting disease-related processes, or in treating the underlying cause of the disease.

For example, Conjugates according to embodiments of the invention, may be used as antisense or siRNA therapy, which is a form of medical treatment, that comprises the administration of a single-stranded or a double-stranded nucleic acid strands (DNA, RNA or a chemical analogue), that bind to a DNA sequence that encodes for a specific protein, or to the respective messenger RNA (mRNA), through which the translation into protein takes place. This treatment may act to inhibit the expression of the respective gene, thereby preventing the production of the respective disease-related protein that may play a role in the etiology or pathogenesis of the disease. Alternatively, the Conjugates of the invention may comprise therapeutic proteins, or protein/nucleic acid complexes, such as the Cas9 protein.

The terms "drug" or "medicament" in the context of the present invention, relate to a chemical substance, that when administered to a patient suffering from a disease, is capable of exerting beneficial effects on the patient. The beneficial effects can be amelioration of symptoms, or counteracting effects of an agent or substance, that play(s) a role in the disease process. The drug may comprise a small molecule or a macromolecule, such as a protein, or single- or double-stranded RNA or DNA, administered to inhibit gene expression. Among others, the drug may comprise siRNA or ASO. In some embodiments, the drug is aimed at treating degenerative disorders, cancer, ischemic, infectious, toxic insults, or immune-mediated disorders.

The term "biological membrane" according to the invention refers to any phospholipid membrane related to a biological system. Examples for such phospholipid membranes are the plasma membrane of cells, intracellular membranes, or biological barriers, such as the blood-brain-barrier (BBB), the blood-ocular-bather (BOB), or the blood-placenta barrier.

Embodiments of the invention provide pharmaceutical compositions, comprising the Conjugates described herein, and pharmaceutically-acceptable carrier(s) or salt(s). According to some embodiments, the Conjugates and pharmaceutical compositions of the invention may be used in vivo, in the clinical setting.

Other embodiments of the invention include Conjugates of the invention, or pharmaceutical compositions comprising Conjugates of the invention, for use for the treatment of medical disorders in a patient in need thereof. Further embodiments of the invention include the use of Conjugates of the invention in the preparation of pharmaceutical compositions for the treatment of medical disorders, in a patient in need thereof. In some embodiments, the medical disorder is cancer.

A Conjugate according to embodiments of the invention may be advantageous in improving the delivery of siRNA, ASO, a therapeutic protein such as an antibody through cell membranes or through biological barriers, such as the Blood-Brain-Barrier (BBB), thus improving the performance of the macromolecule drug in one or more aspects, such as, for example, efficacy, toxicity, or pharmacokinetics.

Important aspects by which the Conjugates of the invention are designed to be advantageous over other drug delivery systems can relate to optimized favorable binding affinity to albumin, that enables, on the one hand, prolonged residence time in the body, while providing wide distribution throughout the body, and conferring protection from degradation by plasma lytic enzymes; while on the other hand, enabling efficacious disengagement of the Conjugate from albumin, for preferential binding to phospholipid cell membranes, with subsequent delivery across the membranes into the cells Another important aspect by which the Conjugates of the invention are designed to be advantageous over other drug delivery systems can relate to their comprising a red-ox-sensitive moiety, i.e., a disulfide group, which provides selective cleavage of the construct in the cytoplasm, with release of the macromolecule drug, to exert its pharmacological effects at its target sites.

In an embodiment of the invention, the drug is a macromolecule, selected from the group consisting of siRNA, ASO or a therapeutic protein.

In an embodiment of the invention, it provides a pharmaceutical composition, comprising a Conjugate of the invention, having the structure as set forth in any of Formulae (II), (III), (IV), (IVa), (V), (Va), (VI), (VII), (VIIa), (VIII) or (VIIIa) and a pharmaceutically-acceptable salt or carrier.

In an embodiment of the invention, it provides a method for delivery of a drug into biological cells, wherein said cells are in culture, or in a living animal, or in a human subject; the method comprising contacting the cells with a Conjugate of the invention.

In an embodiment of the invention, it provides a method wherein the biological membrane is selected from a group consisting of cell membranes, and biological barriers, wherein said biological barriers are selected from the blood-brain-barrier, the blood-ocular-barrier or the blood-fetal-barrier.

In an embodiment of the invention, it provides a Conjugate, where E, E' or E" each having independently the structure as set forth in any of Formulae (II), (III), (IV), (IVa), (V), (Va), (VI), (VII), (VIIa), (VIII) or (VIIIa), attached to a drug.

As mentioned above, the scope of the invention also includes molecules termed "precursors". A "precursor" in the context of the invention, is a molecule that comprises any of moieties E, E' or E" according to any of Formulae (II), (III), (IV), (IVa), (V), (Va), (VI), (VII), (VIIa), (VIII) or (VIIIa), linked to a chemical group, that is destined to be removed or modified during the synthesis of the Conjugate, namely, is removed or modified in the stages of attachment of a D moiety to the E, E' or E" moiety. Examples for such chemical groups are phosphoramidite, azide, acetylene, [Dimethoxytrityl bis-(4-methoxyphenyl) phenyl methyl] (DMT), or N-hydroxysuccinimide (NHS) groups.

In a more specific embodiment of the invention, wherein D is an oligonucleotide drug (e.g. siRNA), the invention provides a precursor, wherein the chemical moieties, destined to be removed or modified during the conjugation of E, E' or E" to D, include phosphoramidite and/or DMT.

Yet another precursor serves for attachment of E, E' or E" to D that is a protein drug. In said precursor, the E, E' or E" moiety is linked to one of the following structures, A or B:

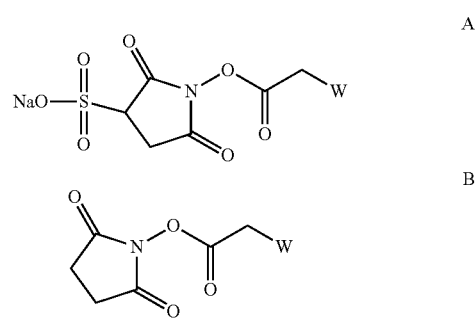

wherein W is selected from E, E' or E" according to any of Formulae (II), (III), (IV), (IVa), (V), (Va), (VI), (VII), (VIIa), (VIII) or (VIIIa). Said precursor is aimed at binding, via its N-hydroxysuccinimide (NHS) moiety, to amine groups of lysine side-chains of the protein.

Embodiments of the invention may further include pharmaceutical compositions, comprising a Conjugate, according to any of Formulae (I), (II), (III), (IV), (IVa), (V), (Va), (VI), (VII), (VIIa), (VIII) or (VIIIa), and a pharmaceutically-acceptable salt or carrier.

The invention also comprises methods for specific inhibition of gene expression, in vitro or in vivo. In one embodiment, the method may include utilization of a Conjugate according to any of Formulae (I), (II), (III), (IV), (IVa), (V), (Va), (VI), (VII), (VIIa), (VIII) or (VIIIa), or a respective pharmaceutical composition, wherein D is siRNA or an ASO, designed to silence the expression of a specific gene. In some embodiments, the gene encodes for a pathogenic protein that has a role in the etiology or pathogenesis of a disease. In some embodiments, D is a therapeutic protein.

In an embodiment of the Invention, it provides a Conjugate, comprising siRNA, linked at each of its ends to an E, E' or E" moiety, according to any of Formulae (II), (III), (IV), (IVa), (V), (Va), (VI), (VII), (VIIa), (VIII) or (VIIIa).

In another embodiment of the Invention, it provides a Conjugate, comprising siRNA, linked at each of its ends, and also at an internal position within the siRNA duplex, to an E, E' or E" moiety, according to any of Formulae (II), (III), (IV), (IVa), (V), (Va), (VI), (VII), (VIIa), (VIII) or (VIIIa).

In yet another embodiment of the Invention, it provides a method for induction of strain and focal structural perturbations in the external leaflet of a phospholipid membrane; said method comprising interacting a Conjugate of the Invention with the phospholipid membrane, wherein the Conjugate comprises an siRNA duplex, linked at each of its ends, and potentially also at an internal position within the siRNA duplex, to E, E' or E" moieties (i.e., 2-3 moieties in total), each having the structure according to any of Formulae (II), (III), (IV), (IVa), (V), (Va), (VI), (VII), (VIIa), (VIII) or (VIIIa).

Due to this structure of the Conjugate of the Invention, the siRNA approaches the membrane parallel to its surface, with the E, E' or E'' moieties oriented towards the membrane core, perpendicular to the membrane surface (demonstrated in FIGS. 1a, 1b and 1c). The resultant proximity of the highly negatively-charged siRNA to the membrane surface thereby induces strain and focal structural perturbations of the external leaflet of the phospholipid membrane. Such induction of external membrane strain and structural perturbations may be useful, among others, for the initiation of endocytosis, or for the induction of passage of a Conjugate harboring the siRNA from one membrane leaflet to the other (flip flop). Both processes are potentially highly-useful for the initiation and/or propagation of trans-membrane delivery of siRNA. Said phospholipid membrane may be any phospholipid membrane, including, without limitation, liposomes or cell membranes, either in vitro or in vivo.

Conjugates according to embodiments of the invention may be used for the treatment of a medical disorder. Embodiments of the invention include methods for medical treatment, comprising the administration to a patient in need therapeutically effective amounts of a pharmaceutical composition, comprising a Conjugate according to any of Formulae (I), (II), (III), (IV), (IVa), (V), (Va), (VI), (VII), (VIIa), (VIII) or (VIIIa); wherein D is a drug useful for treatment of the respective medical disorder.

In one embodiment, the method is for genetic treatment with siRNA or ASO, said method comprising the administration to a patient in need therapeutically effective amounts of a pharmaceutical composition, comprising a Conjugate of the invention, according to any of Formulae (I), (II), (III), (IV), (IVa), (V), (Va), (VI), (VII), (VIIa), (VIII) or (VIIIa); wherein D is siRNA, an ASO or a therapeutic protein, useful in inhibiting the expression of a gene which plays a role in the disease of the specific patient.

In another embodiment of the invention, the invention includes a method for medical treatment of a disease by therapeutic a protein, where D is a protein to be delivered across biological phospholipid membranes into cells, or through biological barriers, such as the blood-brain barrier. Said cells are either in cell culture in vitro, or in a living animal or a human subject in vivo. In some embodiments, the cell is a neoplastic cell. In some embodiments, the neoplastic cell is a tumor cell. In some embodiments, the neoplastic cell is a cell within a metastasis. The cell may be a eukaryotic cell, a eukaryotic cell transfected by an oncogenic agent, a human cell, a cell that is a pre-cancerous cell, or any combination thereof. The cell may be in vitro, i.e., within a cell culture, ex vivo, or in vivo, namely within a living animal or a human subject.

In yet another embodiment of the invention, D is a protein, administered as a replacement therapy, e.g., to replace a mutated, malfunctioning protein, thus addressing a physiological need. In another embodiment, D is a protein that has as role in gene regulation, including, among others, proteins that have a role in DNA or RNA editing (adding, disrupting or changing the sequence of specific genes). In one embodiment, said protein may be a member of the CRISPRs (clustered regularly interspaced short palindromic repeats) related proteins. Specifically, said protein can be or may comprise the Cas9 protein (CRISPR associated protein 9), an RNA-guided DNA nuclease enzyme, or an analogue thereof, potentially loaded with its guide oligonucleotide sequence.

In one of the embodiments of the invention, it describes a method for genetic treatment of a medical disorder, wherein said method comprises administration to a patient in need therapeutically effective amounts of a pharmaceutical composition, comprising a Conjugate according to any of Formulae (I), (II), (III), (IV), (IVa), (V), (Va), (VI), (VII), (VIIa), (VIII) or (VIIIa); wherein D is a CRISPR protein, such as Cas9, administered together with an appropriate guide oligonucleotide, thus achieving delivery of the protein, loaded with a respective guide oligonucleotide into the cells, where the CRISPR protein can exert its genome editing activity. A guide oligonucleotide in this context is a sequence of RNA or DNA that guides the Cas9 protein to a specific locus (place) on the DNA, in order to induce a double-strand DNA cleavage at that site, thus enabling repair of the local defect in the genetic material. In the case of Cas9, the guide oligonucleotide is short segment of RNA, the sequence of which is complementary to the sequence of the target DNA locus.

Therefore, conjugates according to embodiments of the invention, and the respective pharmaceutical compositions, as well as the respective methods, may be beneficial, among others, in the treatment of medical disorders, selected among others, from cancer, toxic insults, ischemic disease, infectious disease, protein storage disease, trauma, immune-mediated disease, or a degenerative disease.

Therefore, an embodiment of the Invention is method for treatment of a medical disorder, said method comprising administration to a patient in need, therapeutically effective amounts of a pharmaceutical composition, that comprises an Conjugate according to any of any of Formulae (I), (II), (III), (IV), (IVa), (V), (Va), (VI), (VII), (VIIa), (VIII) or (VIIIa), where D is drug useful for the treatment of said medical disorder.

According to some embodiments, the medical disorder is cancer. As used herein, the term "cancer" refers to the presence of cells that manifest characteristics that are typical of cancer-causing cells, such as uncontrolled proliferation, loss of specialized functions, immortality, significant metastatic potential, significant increase in anti-apoptotic activity, rapid growth and proliferation rate, or certain characteristic morphology and cellular markers. Typically, cancer cells are in the form of a tumor, existing either locally within an animal, or circulating in the bloodstream as independent cells, as are, for example, leukemic cells.

In the field of neurological disorders, conjugates according to embodiments of the invention may be useful, among others, in the treatment of neurodegenerative disorders, such as Alzheimer's disease, Motor Neuron Disease, Parkinson's disease, Huntington's disease, multiple sclerosis and Creutzfeldt-Jacob disease.

In the field of infectious disorders, conjugates according to embodiments of the invention may be useful, among others, for the delivery of antibiotics or antiviral agents into respective bacteria or viral pathogens. Accordingly, the Conjugates of the invention may have anti-infectious properties, thus being useful for the treatment of infectious diseases, such as bacterial or viral infections.

In other embodiments, the Invention relates to utilization of the Compounds of the Invention to enhance delivery of a chemical compound across phospholipid membranes, into cells. Depending on the attached chemical compound and the desired indication, such delivery can have various useful utilizations. For example, in plants, such delivery can assist in improving crop quality and quantity; among others, by improving plant's genetics, or by eradication of various insects, bacteria or fungi.

Such delivery may also be useful for the delivery of antibiotics or antiviral agents into respective bacteria or viral pathogens. Accordingly, the Conjugates of the invention may have anti-infectious properties, thus being useful for the treatment of infectious diseases, such as bacterial or viral infections. Therefore, an embodiment of the Invention is an E, E' or E", linked to an antiviral or antibacterial drug. Such drug can be, among others, a genetic sequence(s), aimed at interacting with the genetic material of the infectious agent, thus interfering with its replication or metabolism, and affecting its survival.

Conjugates of the Invention, via their properties in delivery across biological membrane can also be useful for treatment of a variety of medical disorders, such as disorders induced by ischemic, toxic, traumatic insults, or medical disorders of genetic etiology of pathogenesis.

EXAMPLES

Some examples will now be described, in order to further illustrate the invention, and in order to demonstrate how embodiments of the invention may be carried-out in practice.

Example 1: A General Method for Synthesis of Conjugates According to Embodiments of the Invention, Wherein D Moieties are Oligonucleotides Initially, a gene to be silenced is chosen, based on its role in the disease etiology or pathogenesis. Then, based on bio-informatic methodologies known in the art, the nucleotide sequences to be incorporated in the Conjugate are designed and determined (typically 19-21 base-pairs double-stranded RNA for a RISC substrate or 25-29 base-pairs double-stranded RNA for a Dicer substrate).

Synthesis is carried-out in the 3' to 5' direction. Solid phase synthesis is applied, using phosphoramidite building blocks, derived from protected 2'-deoxynucleosides (dA, dC, dG, and T), ribonucleosides (A, C, G, and U), or chemically modified nucleosides, e.g. LNA (locked nucleic acids) or BNA (bridged-nucleic-acids). The building blocks are sequentially coupled to the growing oligonucleotide chain, in the order determined by the sequence of the desired siRNA.

Following the construction of the oligonucleotide, one or more E types of the invention are added as part of the building blocks of the oligonucleotide. Initially, the E moiety is added at its precursor form, as described above. A major advantage of the Compounds of the Invention, is that they provide a uniform linkage moiety, as described in Formulae (II), (III), (IV), (IVa), (V), (Va), (VI), (VII), (VIIa), (VIII) or (VIIIa), for linking the E, E', or E" moieties to either the 5'-end of the oligonucleotide, the 3'-end of the oligonucleotide, or at internal position along the oligonucleotide. Among others, such precursor moieties may comprise any protecting group for hydroxyl known in the art, phosphoramidite, azide, acetylene, [Dimethoxytrityl bis-(4-methoxyphenyl) phenyl methyl] (DMT), N-hydroxysuccinimide (NHS) groups. Upon completion of the assembly of the chain, the product is released from the solid support into solution, de-protected, and collected. The desired Conjugate is then isolated by high-performance liquid chromatography (HPLC), to obtain the desired conjugated oligonucleotide in high purity. In the case of siRNA, each of a complementary RNA strands is synthesized separately, and then annealing of the two strands is performed in standard conditions as known in the art, to yield the desired double-stranded siRNA.

Example 2: A Method for Synthesis of Sterol 1; the Common Building Block of the E Moieties of the Invention The starting material, perfluoro-tertbutanol is commercially-available. The synthesis starts from estradiol, and is performed according to Scheme 1:

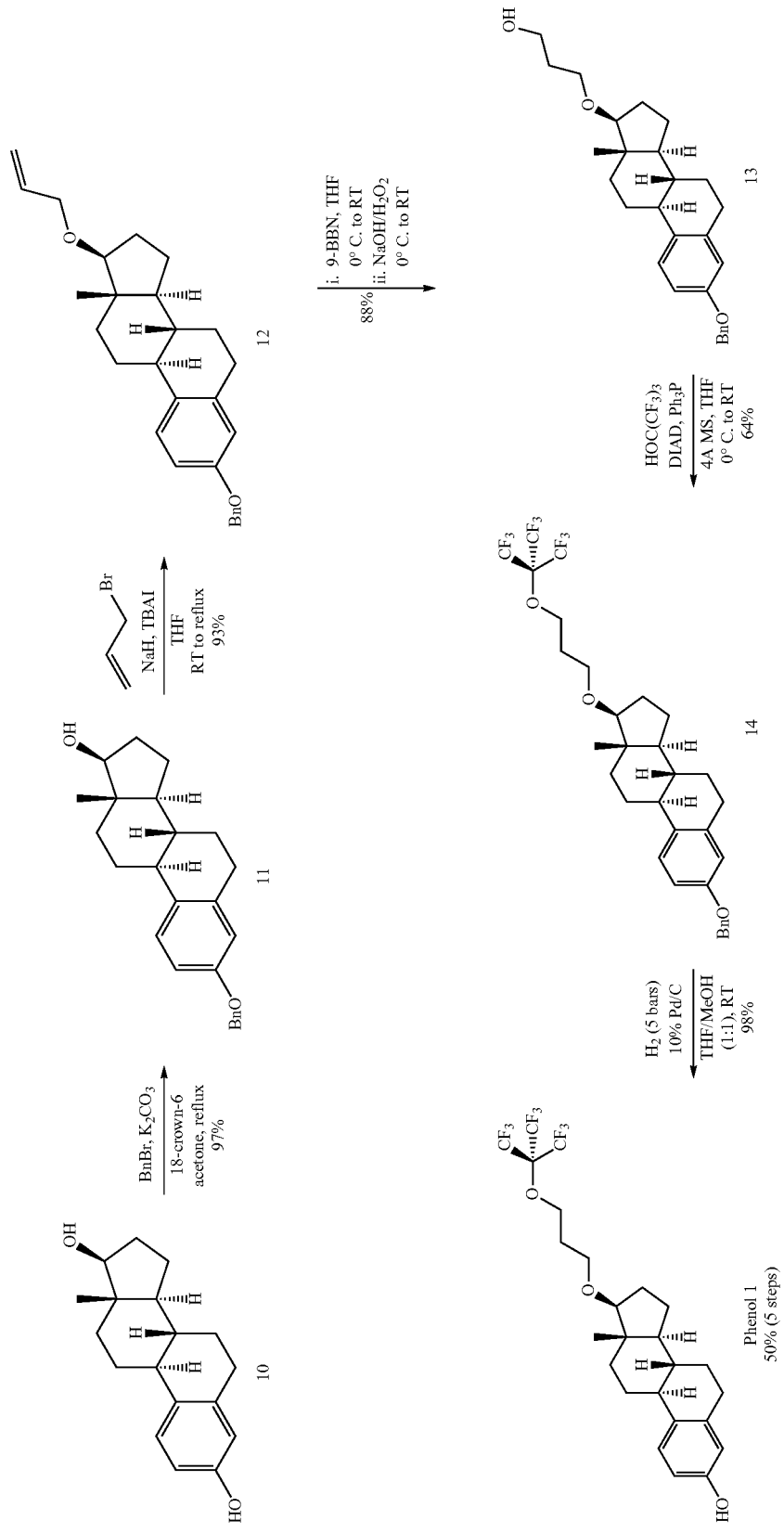

Estradiol was protected by a benzyl group to provide compound 11. Allylation of alcohol 11 (25.6 g) under optimized reactions conditions (allyl bromide, NaH, cat. Tetra-n-butylammonium bromide (TBAI), tetrahydrofuran (THF), reflux, 16 h) afforded allyl ether 12 (21.85 g, 77%) as a white solid (purified by successive trituration in heptane and MeOH). Regio-selective hydroboration of the terminal alkene (21.8 g) with 9-Borabicyclo[3.3.1]nonane (9-BBN), upon standard oxidative workup (NaOH/H$_2$O$_2$) provided alcohol 13. Mitsunobu reaction of the alcohol 13 (13.6 g) with excess perfluoro-tert-butanol under optimized reaction conditions [Diisopropyl azodicarboxylate (DIAD), PPh$_3$, 4 A molecular sieve (MS), THF, RT, 16 h] afforded the desired ether 14. Compound 14 was subjected to catalytic hydrogenation (10% Pd/C, RT) using a mixture (1:1) of THF and 2,2,2-trifluoroethanol as solvent (5 bars, Parr reactor) to afford (after ~18 h) the phenol 1 as off-white solid.

Example 2: A Method for Synthesis of Apo-Si-K-93-A-Precursor

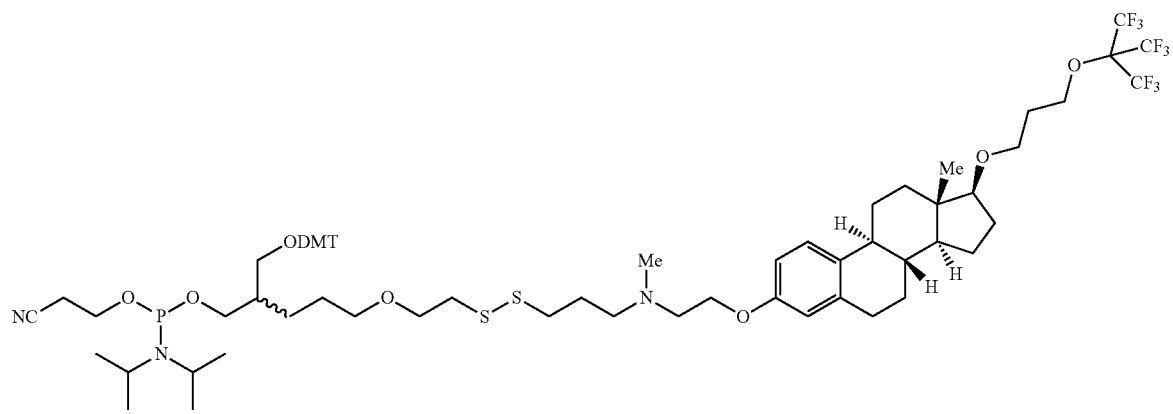

Apo-Si-K-93-A-Precursor

Synthesis of Amine 7:

Scheme 1. Synthesis of amine 7.

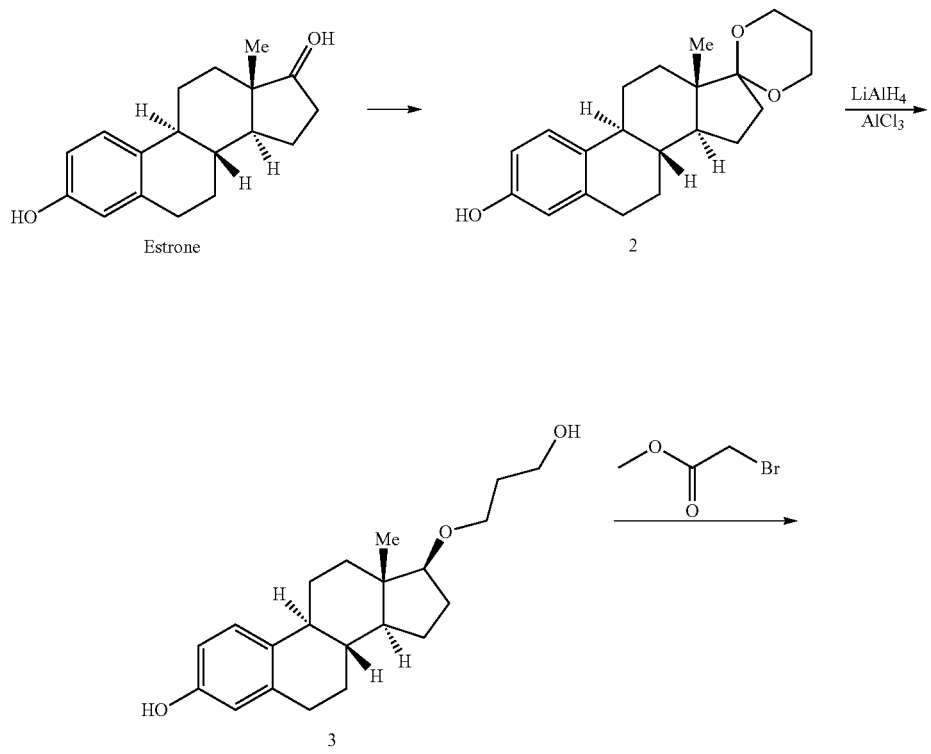

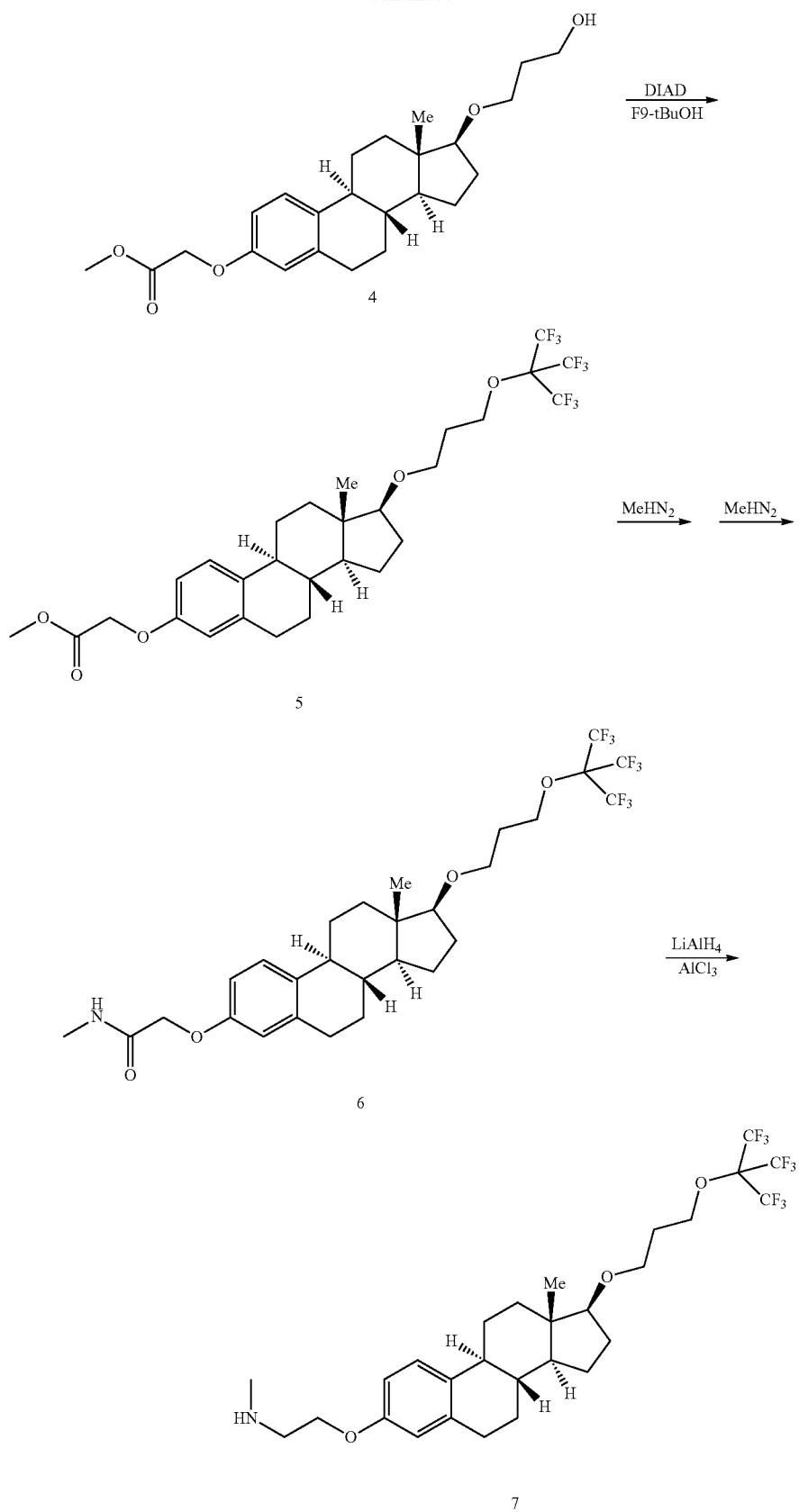

Estrone was treated propanediol and trimethyl orthoformate to provide compound 2. Treatment with LiAlH$_4$ and AlCl$_3$ provided the ring-opened product 3. The phenol was alkylated with methyl bromoacetate and compound 4 was obtained. The perfluoro-tert-butanol moiety was introduced using Mitsunobu conditions (compound 5). Compound 5 was treated with methylamine to provide amide 6. Reduction of the amide using BH$_3$.DMS provided amine 7.

Synthesis of Thiotosylate 14:

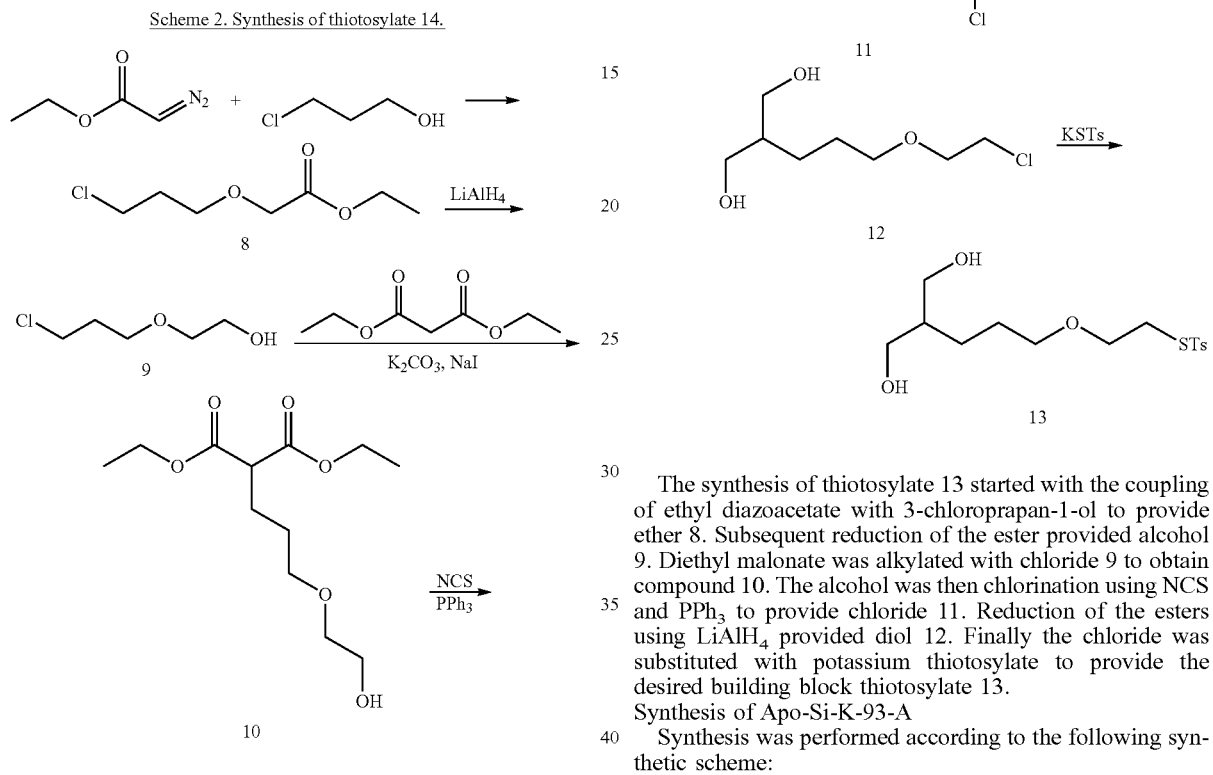

The synthesis of thiotosylate 13 started with the coupling of ethyl diazoacetate with 3-chloroprapan-1-ol to provide ether 8. Subsequent reduction of the ester provided alcohol 9. Diethyl malonate was alkylated with chloride 9 to obtain compound 10. The alcohol was then chlorination using NCS and PPh$_3$ to provide chloride 11. Reduction of the esters using LiAlH$_4$ provided diol 12. Finally the chloride was substituted with potassium thiotosylate to provide the desired building block thiotosylate 13.

Synthesis of Apo-Si-K-93-A

Synthesis was performed according to the following synthetic scheme:

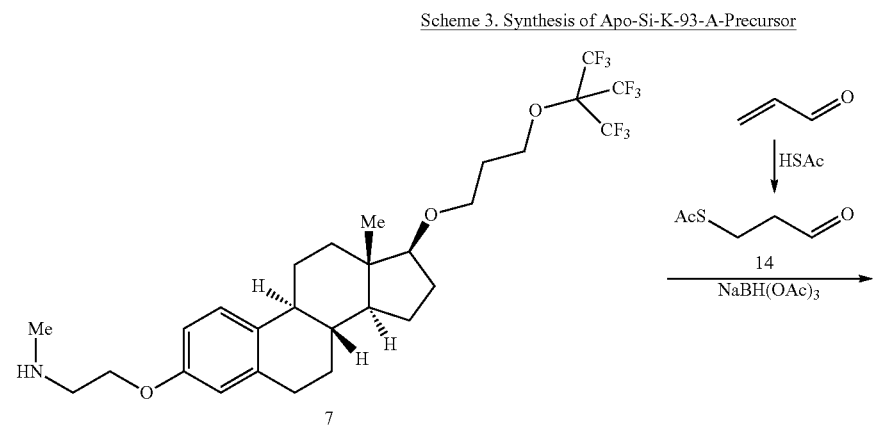

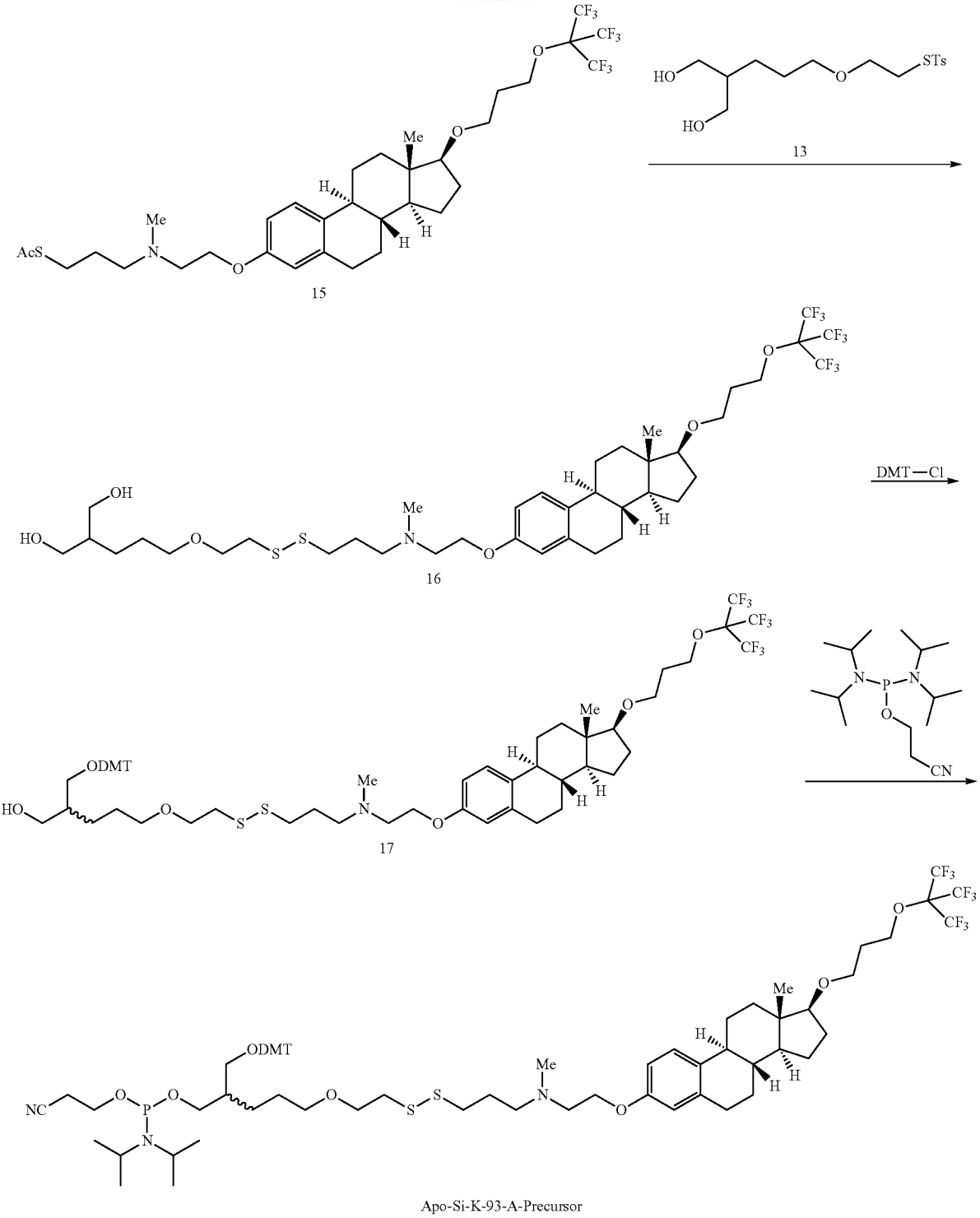

Apo-Si-K-93-A-Precursor

Amine 7 was alkylated with 1-bromo-3-chloropropane, but we found these conditions resulting in rather poor yields. However, when we did the reductive amination with acrolein derived thioaldehyde 14 much better yields were obtained and also the necessity of thioacetate exchange was removed from the overall synthesis. Acrolein was treated with thioacetic acid in presence of base to provide good conversion. The desired material was isolated using flash chromatography in 55% yield. Subsequent reductive amination with aldehyde 14 gave compound 15 in 59% yield.

Sodium methoxide in methanol was added to a solution of thioacetate 15 and thiotosylate 13, which removed the acetate from 15 allowing the resulting thiol to react with 13 to form the desired asymmetric disulfide (16). Compound 16 was reacted with DMT-C$_1$ to provide mono-protected diol 17. Reaction with the suitable phosphoramidite-agent afforded Apo-Si-K-93-A. Purification of the acid-labile phosphoramidite product was done using flash chromatography with silica that had been pretreated with $Et_3N$. Eventually 4×220 mg was made.

Experimental Section (8R,9S,13S,14S)-13-Methyl-6,7,8,9,11,12,13,14,15,16-decahydrospiro[cyclopenta[a]phenanthrene-17,2'-[1,3]dioxan]-3-ol (2)

To a suspension of estrone (67.9 gram, 0.251 mol) in toluene (300 mL) were added 1,3-propanediol (70 mL) and trimethyl orthoformate (100 mL). The suspension was treated with pTsOH (1 gram, 5 mmol) and warmed to 60° C. for 16 h. After cooling to room temperature, triethyl amine (10 mL) and water (100 mL) were added and stirring continued for 30 min. The phases were separated and the organic phase was washed with water (2×100 mL) and brine, dried over $Na_2SO_4$ and concentrated. The crude material was dissolved in toluene (150 mL) and further diluted by slow addition of heptane (750 mL) causing the formation of white precipitate. The solids were filtered off and dried in vacuo. Compound 2 (71.1 gram, 217 mmol) was isolated as a white solid in 86% yield.

(8R,9S,13S,14S,17S)-17-(3-hydroxypropoxy)-13-methyl-7,8,9,11,12,13,14,15,16,17-decahydro-6H-cyclopenta[a]phenanthren-3-ol (3)

To a solution of compound 2 (71.4 gram, 217 mmol) in THF (1.5 L) at 0° C. were added carefully $LiAlH_4$ (10 gram, 263 mmol) and $AlCl_3$ (116 gram, 872 mmol). The exothermic reaction was allowed to stir an additional 30 min at 0° C., then the solids were warmed to 50° C. while mechanically stirring (using a rotavap) for 3 h. The mixture was cooled to 0° C. and aqueous saturated ammonium chloride (150 mL) was added dropwise. The mixture was stirred for an additional 30 min, then filtered over a short path of silica the solids were washed with ethyl acetate. The organic layers were collected and washed with brine, dried over $Na_2SO_4$ and concentrated. The crude material (89.2) was predominantly compound 3, but purification was performed after the next step.

Methyl 2-(((8R,9S,13S,14S,17S)-17-(3-hydroxypropoxy)-13-methyl-7,8,9,11,12,13,14,15,16,17-decahydro-6H-cyclopenta[a]phenanthren-3-yl)oxy)acetate (4)

The crude material 3 (89.4 gram) was dissolved in acetone (1.25 L) and MeOH (0.2 L) and treated with potassium carbonate (60 gram, 435 mmol) and methyl bromoacetate (50 mL, 435 mmol). The suspension was warmed to 60° C. and stirring continued for 16 h. Based on TLC, all phenolic moieties had been alkylated. The mixture was cooled to room temperature and filtered. The filtrate was concentrated and further purified using flash chromatography (eluent 20% to 30% EtOAc in heptane, removing all impurities, 100% EtOAc to obtain the desired material).

Compound 4 (56.7 gram, 140.3 mmol) was isolated as a yellow oil in 65% yield.

Methyl 2-(((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)acetate (5)

To a solution of compound 4 (56.7 gram, 140.3 mmol) in THF (1 L) were added triphenylphosphine (55.4 gram, 211 mmol), nonafluoro-tert-butyl alcohol (30 mL) and di-tert-butyl azodicarboxylate (38.5 gram, 167 mmol). The mixture was stirred for 30 min when TLC showed full conversion. Heptane (500 mL) was added and the mixture was partially concentrated to ~0.500 mL. More heptane (1 L) was added and the mixture was stirred overnight at room temperature. Precipitates had formed and were filtered off, the filtrate was concentrated to provide compound 5 as yellow syrup, albeit contaminated with traces of DBAD and triphenylphosphine.

2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)-N-methylacetamide (6)

The crude syrup of compound 5 was diluted with MeOH (250 mL) and 40% aqueous methylamine (350 mL) was added. The white precipitate was stirred for 1 h when TLC showed full conversion. Water (1 L) was added and the solids were filtered off. The residue was washed with water and taken up in dichloromethane (1 L). The organic layer was washed with brine, dried over $Na_2SO_4$ and concentrated. Further purification was performed using ca 7 cm of silica and initial elution with 15% EtOAc in heptane. When all impurities were removed from the column, compound 6 was eluted with 100% EtOAc. Compound 6 (82.0 gram, 132 mmol) was isolated as a white solid in 94% yield, albeit traces of triphenylphosphoxide remained present.

2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)-N-methylethan-1-amine (7)

To a solution of compound 6 (56.0 gram, 90.5 mmol) in THF (500 mL) at 65° C. was added dropwise $BH_3.DMS$ (56 mL, 590 mmol). Refluxing continued for an additional 5 h, then the mixture was cooled to room temperature. The mixture was carefully dissolved in MeOH (300 mL) and 4 M dioxane in HCl (50 mL) was added. The solution was refluxed for 30 min, then cooled to room temperature and concentrated. The mixture was dissolved in MeOH (300 mL) and refluxed for 30 min. After cooling and concentration, the syrup was taken up in $CH_2Cl_2$ (1 L) and washed with aqueous saturated sodium bicarbonate (2×). The organic layer was dried over $Na_2SO_4$ and concentrated. Compound 7 (50.0 gram, 82.6 mmol) was isolated as a clear oil which slowly solidified in 91% yield. The impurity-profile with traces of triphenylphosphoxide was similar to compound 6.

Synthesis of Thiotosylate 13:

Ethyl 2-(3-chloropropoxy)acetate (8)

To a solution of 3-chloropropan-1-ol (20 mL, 239 mmol) in $CH_2Cl_2$ (250 mL) was added at 0° C. ethyl diazoacetate (25 mL, 239 mmol). Then, $BF_3.OEt_2$ (0.30 mL, 2.39 mmol, 0.01 eq.) was added, after which the ice-bath was removed and the mixture was warmed to 37° C. and stirred at that temperature until gas development had ceased (2 hours). The mixture was washed with $H_2O$ (250 mL) and brine (250 mL), dried over $Na_2SO_4$, and concentrated to provide ether 8 (44 g, 240 mmol, quant.) as a yellow oil.

2-(3-chloropropoxy)ethan-1-ol (9)

To an ice-cooled suspension of $LiAlH_4$ (12 g, 316 mmol) in $Et_2O$ (750 mL) was added a solution of ester 8 (57 g, 316 mmol) slowly and the resulting mixture was stirred at room temperature overnight. The reaction was quenched by the addition of KOH (aq. 20% 51 mL) slowly at 0° C. The mixture was stirred at room temperature for 30 minutes, after which it was filtered over Celite. The filtrate was dried over $Na_2SO_4$ and concentrated to afford alcohol 9 (33 g, 240 mmol, 76%) as a clear oil.

Diethyl 2-(3-(2-hydroxyethoxy)propyl)malonate (10)

To a solution of diethyl malonate (25 mL, 166 mmol) and alcohol 9 (23 g, 166 mL) in DMF (500 mL) was added $K_2CO_3$ (34 g, 249 mmol) and NaI (25 g, 166 mmol) and the resulting mixture was stirred at 90° C. for 64 hours. $H_2O$ (1.5 L) was added and the mixture was extracted with EtOAc (3×500 mL). The combined organic layers were washed with brine, dried over $Na_2SO_4$, and concentrated. The crude material was purified using column chromatography (EtOAc:heptane 1:1) to provide product 10 (17 g, 65 mmol, 39%) as a clear yellowish oil.

Diethyl 2-(3-(2-chloroethoxy)propyl)malonate (11)

To a solution of alcohol 10 (17 g, 65 mmol) in $CH_2Cl_2$ (500 mL) was added $PPh_3$ (26 g, 98 mmol) and N-chlorosuccinimide (11 g, 78 mmol) and the resulting mixture was stirred overnight at room temperature. Heptane (300 mL) was added and the mixture was concentrated partially. The formed solids were filtered off and the filtrate was concentrated. The crude material was purified using column chromatography (20% EtOAc in heptane) to provide chloride 11 (14 g, 49 mmol, 75%) as a clear oil.

2-(3-(2-chloroethoxy)propyl)propane-1,3-diol (12)

To an ice-cooled suspension of $LiAlH_4$ (7.3 g, 192 mmol) in $Et_2O$ (500 mL) was added a solution of diethylester 11 (27 g, 96 mmol) slowly and the resulting mixture was stirred at room temperature overnight. The reaction was quenched by the addition of KOH (aq. 20% 31 mL) slowly at 0° C. The mixture was stirred at room temperature for 30 minutes, after which it was filtered over Celite. The filtrate was dried over $Na_2SO_4$ and concentrated to afford diol 12 (14 g, 73 mmol, 76%) as a clear oil.

S-(2-((5-hydroxy-4-(hydroxymethyl)pentyl)oxy) ethyl) 4-methylbenzene-sulfonothioate (13)

To a solution of diol 12 (14 g, 73 mmol) were added potassium thiotosylate (25 g, 110 mmol) and TBAI (2.7 g, 7.3 mmol) and the resulting mixture was stirred at 80° C. for 64 h. The mixture was concentrated and the crude material was purified using column chromatography (40% Acetone in heptane) to provide thiotosylate 13 (5.0 g, 14 mmol, 20%) as a yellow oil.

Synthesis of Apo-Si-K-93-A

S-(3-Oxopropyl) ethanethioate (14)

To a solution of acrolein (11 gram, 196 mmol) in dichloromethane (250 mL) were added triethylamine (6.9 mL, 49 mmol) and thioacetic acid (13.8 mL, 195 mmol). The mixture was stirred overnight at room temperature, then concentrated. Further purification using flash chromatography (15% EtOAc in heptane) provided compound 14 (14.4 gram, 109 mmol) as a brown oil in 55% yield.

S-(6-(((2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino) hexyl) ethanethioate (15)

To a solution of 7 (20.6 gram, 34 mmol) in 1,2-dichloroethane (500 mL) were added acetic acid (8.2 mL, 136 mmol), aldehyde 14 (5.4 gram, 41 mmol) and after 1 min sodium triacetoxyborohydride (30 gram, 141 mmol). The mixture was stirred for 2 h at room temperature, then dichloromethane was added and the mixture was washed with 1M NaOH, water and brine. The organic layer was dried over $Na_2SO_4$ and concentrated. Further purification using flash chromatography (gradient 15% to 25% acetone and 0.1% $Et_3N$ in heptane) provided compound 15 (14.4 gram, 20 mmol) was isolated as a clear oil in 59% yield.

2-(3-(2-((3-((2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino) propyl)disulfanyl)ethoxy)propyl)propane-1,3-diol (16)

A solution of thioacetate 15 (1.9 g, 2.6 mmol) and thiotosylate 13 (1.8 g, 5.1 mmol, 2 eq.) in a $CH_2Cl_2$ (200 mL) and methanol (20 mL) was treated with 5.4 M NaOMe in MeOH (1.42 mL, 7.7 mmol, 3 eq.). The mixture was stirred overnight at room temperature. The mixture was washed with $NaHCO_3$ (200 mL) and brine (200 mL), dried over sodium sulfate, and concentrated. Further purification using flash chromatography (30% acetone+1% $Et_3N$ in heptanes) provided compound 16 (1.2 g, 1.4 mmol, 53%) as yellowish oil.

2-((bis(4-Methoxyphenyl)(phenyl)methoxy)methyl)-5-(2-((3-((2-(((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino) propyl)disulfaneyl)ethoxy)pentan-1-ol (17)

To a solution of 16 (1.2 g, 1.4 mmol) were added $Et_3N$ (0.14 mL, 1.4 mmol, 1 eq.) and DMAP (16 mg, 0.14 mmol, 0.1 eq.). To the resulting mixture DMT-$C_1$ (0.47 g, 1.4 mmol, 1 eq.) was added. The resulting yellow mixture was stirred overnight at room temperature, after which it was concentrated. Purification by column chromatography (20% acetone and 1% $Et_3N$ in heptane) provided monoprotected alcohol 17 (1.0 g, 0.87 mmol, 63%) as a clear yellowish oil.

2-((bis(4-Methoxyphenyl)(phenyl)methoxy)methyl)-5-(2-((3-((2-(((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino) propyl)disulfaneyl) ethoxy)pentyl (2-cyanoethyl) diisopropylphosphoramidite (Apo-Si-K-93-A)

To a solution of monoprotected diol 17 (1.0 g, 0.87 mmol) in dichloromethane (40 mL) was added 2-cyanoethyl N,N,N',N'-tetraisopropylphosphorodiamidite (0.4 mL, 1.25 mmol, 1.3 eq.) and a 0.5 M solution of N-methylmorpholine and 0.25 M trifluoroacetic acid in dichloromethane (2.5 mL, 1 equivalent of N-methylmorpholine to the phosphoramidite-agent). The yellowish solution was stirred for 2 h at room temperature. TLC indicated incomplete conversion, so an additional 0.2 mL of 2-cyanoethyl N,N,N',N'-tetraisopropyl phosphorodiamidite was added. After 1 h the mixture was quenched with aqueous saturated sodium bicarbonate and stirred for an additional 10 minutes. The organic layer was separated, dried over sodium sulfate and concentrated. Further purification using flash chromatography (15% acetone and 1% $Et_3N$ in heptane) provided compound Apo-Si-K-93-A (880 mg, 0.64 mmol, 74%) as a colorless oil.

Example 4: Mode of Linkage of an E Moiety of the Invention, at an Internal Position within an Oligonucleotide Chain Initially, the E moiety is as its precursor form, wherein its two hydroxyl groups are protected by each of DMT [Dimethoxytrityl bis-(4-methoxyphenyl) phenylmethyl]; and phosphoramidite. Customarily, synthesis of the oligonucleotide is carried-out by sequential addition of protected nucleotides at the 3' to 5' direction. The phosphoramidite is used for linkage to the hydroxyl group at the 5'-end of the oligonucleotide chain; then the DMT is removed, and the respective hydroxyl group is linked to the phosphoramidite moiety attached at the 3'-hydroxyl of the next nucleotide to be incorporated into the chain. Following completion of synthesis, of both the Sense (Passenger) and the Guide (Antisense) strands of the siRNA, an annealing procedure takes place, as known in the art, to provide the final, RNA Duplex Conjugate of the Invention. For optimization of performance of the siRNA, the E moiety at the internal position is linked to the Sense (Passenger) strand, since this strand is removed within the RISC Complex, thus enabling the Guide (Antisense) strand to act in the RISC gene silencing apparatus in an uninterrupted manner.

Example 5: Red-Ox-Mediated Detachment and Removal of the E Moiety within the Cytoplasm, to Release the Cargo Drug (e.g., siRNA)

While the E, E' or E" Moieties of the invention are mandatory for the trans-membrane passage of siRNA Conjugates, it is desirable to remove these moieties once the Conjugate reaches the cytoplasm, and excrete them from the body. In the case that the cargo drug is siRNA, this may be beneficial for avoidance of steric interference in the interaction of the siRNA with the gene silencing protein complexes (Dicer and RISC). In addition, such detachment of the cargo drug from the E moieties would minimize burden of Conjugates on cellular phospholipid membranes, thus being potentially advantageous from the safety perspective. For this purpose, all E moieties of the Invention comprise a disulfide moiety. In oxidative conditions, such as those that prevail in the extracellular environment, the disulfide moiety manifests stability, thus enabling, upon its systemic administration in vivo, the Conjugate to distribute in the body, and cross cellular phospholipid membranes into cells. By contrast, the cytoplasm is a highly reductive environment, mainly due to its high concentrations of glutathione, which manifests a cytoplasm/extracellular space concentration gradient of about 4-orders of magnitude. Due to these remarkable reductive conditions within the cytoplasm, disulfide groups of E moieties undergo reduction in the cytoplasmatic milieu. Consequently, there is release of the Cargo drug (e.g., siRNA), to exert its pharmacological activities at its target sites in the cytoplasm (e.g., at the Dicer or RISC protein complexes for gene silencing). Concurrently, the E moieties of the Invention, having a sterol backbone, are excreted from the body via the bile and/or the urine, similar to other sterol-based molecules (e.g., estrogens), either directly or following metabolism (e.g., cytochrome-P-450-mediated metabolism in the liver).

Example 6: An Exemplary Structure of a siRNA Conjugate of the Invention, Comprising Three E Moieties, Each Having the Structure, as Set Forth in Formula (IVa), and its Respective Mode of Action The Conjugate is described in FIGS. 2a, 2b, 2c and 2d. Initially, the Conjugate is in oxidative conditions, and thus it comprises disulfide moieties. Exemplified is a Dicer substrate, wherein the RNA strands are of length of 25 and 27 nucleotides. The longer strand (the Guide, Antisense strand) has a 2 nucleotide over-hang at its 3'-end, required for its binding to the enzyme. In addition, the Sense (Passenger) strand has a free-phosphate at its 5'-end, in order to occupy a respective binding pocket in the enzyme, that is paved by positively charged amino acids. Two of the E moieties are linked to the passenger strand: one at its 5'-end, and the second at about the middle of the strand. The third E moiety is linked to the 5'-end of the Guide. Initially, the Conjugate is the oxidative conditions characteristic of the extracellular space, and thus disulfide groups of the E moieties are preserved. Upon entry into the cytoplasm, due to the ambient reductive conditions, the disulfide bonds are reduced, and the E moieties are cleaved from the RNA, to be excreted form the body, each leaving a small residual stump (FIG. 2b). The Dicer enzyme then cleaves the RNA Duplex, generating a 21/23-nucleotide-long Duplex, thereby also removing the stump on the Guide strand (FIG. 2c). The RNA Duplex is then ready to enter the cytoplasmatic RNA-induced silencing protein complex (RISC). First acts the enzyme Helicase that performs removal of the Passenger strand, including the two residual stumps that are attached to it. Consequently (FIG. 2d), the Guide strand is delivered, intact, into the RISC Complex, to interact with the mRNA encoding for the target protein, thus leading to its degradation, and thereby inducing the desired gene silencing.

Example 7: Biological Performance of Apo-Si-K-93-A

The biological performance of Apo-Si-K-93-A was evaluated in the following aspects, which are all important for the projected utilization of conjugates that comprise this E moiety in vivo, in the clinical setting. For these experiments, two siRNA Duplexes were utilized, each being a Dicer's substrate, designed to silence the EGFP gene. In one of the Duplexes, an Apo-Si-K-93-A moiety was attached to each RNA strand, at its 5'-end (this Duplex was designated K-93-A. In the second duplex, an Apo-Si-K-93-A moiety was attached at the 5'-end of each RNA strand, while a third Apo-Si-K-93-A moiety was attached at an internal position along the passenger (Guide) strand At the site of the 14$^{th}$ nucleotide. This duplex was therefore designated K-93-A-del-14. The nucleotide sequences for each of these constructs were as follows:

1. K-93-A Construct:

```
Sense:
5'-phos/iApo-Si-K93-A/ mAmCrCmCrUmGrArArG rUrUmCrA mUrCmUrG mC rArC rCrArCmCG rUrCrA.

Antisense:
/5'-phos/iApo-SiK-93-A/ rCrGmGrUrGrGrUrGmCrAmGrAmUrGrArArCrU rG mGrGmUmCmA.
```

2. K-93-A-del-14:

```
Sense:
/5phos/iApo-Si-K-93-A/ mAmCrCmCrUmGrArArGrUrUmCrA/ iApo-SiK93-A/rCmUrG mCrArCrCrArCmCG.

Antisense:
/5phos/iApo-Si-K-93-A/
```

-continued
rCrGmGrUrGrGrUrGmCrAmGrAmUrGrArArCrU rUrCrArG mGrGmUmCmA.
r means ribose; m means methylation.

Both Conjugates were then subjected to the following assessments:
1. Protein-Free Fraction Upon Incubation with Albumin:

In order to perform upon administration into the blood, it is valuable for a drug to have both a fraction that is bound to the blood proteins, and a free-fraction, free to migrate through the extracellular space into the cells. In order to examine this aspect for Apo-Si-K-93-A, gel electrophoresis was employed: 20 pmole of RNA samples were diluted in Tris buffer ph=7.4, and bovine serum albumin (BSA) was added to a final concentration of 2 mg/ml. All samples were incubated over night at 25° C. These RNA Samples were then loaded on 12% native poly acryl amid gel, and migrated on electrical field for 1 hour in 5V/cm (bio-rad mini protean). Control samples included RNA samples diluted in water rather than in BSA, and reactions mixtures that were treated with Proteinase K (Sigma) for 2 hr at 37° C., which is aimed at releasing protein-bound conjugate, via albumin proteolysis. Apo-Si-S1, an Apo-Si Conjugate that binds strongly to albumin was used as positive control
2. Cleavage of the Disulfide Moiety of Apo-Si-K-93, Upon Incubation with Reduced Glutathione:

One of the hallmarks of the design of Apo-Si-K-93-A was incorporation of a disulfide group within the Apo-Si-K-93-A moiety, aimed to undergo cleavage selectively in the reductive conditions that prevail within the cytoplasm, thus releasing the cargo genetic drug to interact with the cytoplasmatic gene silencing complexes: Dicer and RISC. In order to demonstrate this feature of Apo-Si-K-93-A, 20 pmole of RNA samples were diluted in 30 mM Tris buffer ph=7.4, supplemented with 1 mM of Glutathione (Sigma). All samples were incubated for 2 hours at 37° C. Control samples were diluted in water. RNA Samples were then loaded on 12% native poly acryl amid gel and migrated on electrical field for 1 hour in 5 V/cm (bio-rad mini protean).
3. Delivery into Cells and Gene Silencing In Vitro:

HeLa-EGFP cell line obtained from Cell Biolabs was grown in Dulbecco's modified Eagle's medium (Gibco), supplemented with 10% FBS (Gibco), 100 U/ml penicillin 100 mg/ml streptomycin (Biological Industries, Israel) and blasticidin 10 µg/ml. Cells maintained in a 37° C. incubator with 5% CO2 humidified air. One day before transfection, cells (40,000 cells/well) were plated on 24 well black-plate glass bottom with complete medium without the supplement of antibiotics. The following day, cells were exposed to MNM-conjugates; either 600 nM of the Conjugate, incubated with 10% BSA for 72 hours; or incubation with 10, 40 and 150 nM of the Conjugate, in serum-free conditions for 24 hours, followed by addition of complete serum for additional 48 hours of incubation. Protein down-regulation was therefore measured at 72 hours post transfection, when medium was aspirated, and the cells were washed with HBSS. EGFP fluorescence intensity was quantified by the infinite M200—Pro Multimode Reader (Tecan), excitation wavelength 488 nm, emission wavelength 535 nm.
Results:

FIG. 3 demonstrates protein-free fraction upon incubation with BSA. In contrast to Apo-Si-S1, that interacted completely with the BSA, K-93-A, and K-93-A-del-14 showed only minor interaction with BSA and revealed a major free fraction, that interestingly, was not eliminated significantly by the presence of an additional K-93-A moiety, in K-93-A-del-14 (Apo93-del-14) (Arrow). Treatment of proteinase K (PK) recovered all protein-bound Apo-Si-S1, and also released the small fraction of the K-93-A that attached to BSA in both K-93-A and K-93-A-del-14 conjugates.

FIG. 4 demonstrates that incubation of both K-93-A and K-93-A-del-14 conjugates with reduced glutathione (1 mM for 2 hours) led to a robust cleavage of both K-93-A and K-93-A-del-14 conjugates (Arrow) Importantly, the attachment of the third E moiety did not slow-down the reduction reaction. The reaction took place in the relatively mild exposure conditions to the reductive agent (1 mM, 2 hours). These positive results were in alignment with the observed effects on gene silencing: K-93-A and K-93-A-del-14, attached to the same EGFP siRNA sequences, induced marked knock-down of EGFP expression, in both serum-free and serum+ conditions, in a dose-dependent manner. With serum (10% BSA), 600 nM of K-93-A induced 24.1±5.0% down-regulation of the EGFP gene, while the addition of the third, internal, E moeity moiety was associated with a marked enhancement of the observed gene silencing to 50.3%±5.0%. Efficacious gene silencing were observed also in the serum-free conditions, where K-93-A induced gene silencing of 63.5%, 79.3%, and 86.3%, upon incubation with 10 nM, 40 nM, and 150 nM of the Conjugate, respectively. K-93-A-del-14 induced 503%, 76.6% and 84.7%, gene silencing upon treatment with 10 nM, 40 nM, and 150 nM, respectively.
Conclusions:

As evaluated in HeLa cells in vitro, Apo-Si-K-93-A manifested a favorable performance profile, that merits its continued development as a delivery tool for siRNA, across biological membranes into cells. This E moiety manifested a large free fraction upon incubation with albumin, robust reduction and cleavage of the disulfide moiety in glutathione levels that correspond to the physiological levels within the cytoplasm of living cells, culminating in efficacious gene silencing, in both the presence and absence of plasma proteins Importantly, Apo-Si-K-93-A manifested cooperativity in its activity, as reflected by the attachment of three moieties, which was found clearly superior over attachment of two moieties, in the desirable induction of gene silencing.

Example 7: Biological Performance of Apo-Si-K-63-A

Two siRNA Duplexes were utilized, each being a Dicer's substrate, designed to silence the EGFP gene. In one of the Duplexes, an Apo-Si-K-63-A moiety was attached to each RNA strand, at its 5'-end (this Duplex. This Duplex was designated K-63-A. In the second Duplex, an Apo-Si-K-63-A moiety was attached at the 5'-end of each RNA strand, while a third Apo-Si-K-63-A moiety was attached at an internal position along the passenger (Guide) strand At the site of the $14^{th}$ nucleotide. This duplex was therefore designated K-63-A-del-14. The nucleotide sequences for each of these constructs were as follows:
1. K-63-A Construct:

Sense:
5'-phos/iApo-Si-K63-A/ mAmCrCmCrUmGrArArG rUrUmCrA mUrCmUrG mC rArC rCrArCmCG rUrCrA

-continued

```
Antisense:
/5'-phos/iApo-SiK-63-A/ rCrGmGrUrGrGrUrGmCrAmGrAmUrGrArArCrU rG mGrGmUmCmA
```

2. K-63-A-del-14 Construct:

```
Sense:
/5phos/iApo-Si-K-63-A/ mAmCrCmCrUmGrArArGrUrUmCrA/ iApo-SiK63-A/rCmUrG mCrArCrCrArCmCG

Antisense:
/5phos/iApo-Si-K-63-A/ rCrGmGrUrGrGrUrGmCrAmGrAmUrGrArArCrU rUrCrArG mGrGmUmCmA
```

Study Objectives:

Assessment of the performance of both Constructs, in silencing the expression of the EGFP gene:

Methods:

HeLa-GFP cell lines were obtained from Cell Biolabs. Cells were grown in Dulbecco's modified Eagle's medium (Gibco) supplemented with 10% FBS (Gibco), 100 U/ml penicillin 100 mg/ml streptomycin (Biological Industries, Israel) and blasticidin 10 µg/ml. cells maintained in a 37° C. incubator with 5% CO2 humidified air. The day before transfection, cells were plated (40,000 cells/well) on 24-well black-plate glass bottom. The following day, cells were exposed to K-63-A or K-63-A-del-14, in the presence of 10% serum. For serum-free transfections, medium was aspirated, and cells were washed with Hank's Balanced Salt Solution (HBSS), and medium was then replaced with serum free Opti-MEM (Thermo Fisher Scientific), for 24 hours, followed by addition of serum for incubation for additional 48 hours. Down-regulation of protein expression was measured 72 hours post transfection. For this purpose medium was aspirated, and cells were washed with HBSS. EGFP fluorescence intensity was quantified by the infinite M200—Pro Multimode Reader (Tecan), excitation wavelength 488 nm, emission wavelength 535 nm.

Results:

Both K-63-A, harboring two E moieties, and K-63-A-del-14, harboring three E moieties induced efficacious knockdown of the expression of RGFP.

In the presence of serum, 600 nM of K-63-A reduced EGFP expression to 77.6%±1.3 (mean±SD). A stronger effect was observed with K-63-A-del-14, where 600 nM reduced EGFP expression to 60.2%±1.0.

In serum-free conditions, a robust GFP knockdown was induced by the Conjugates of the Inventions: K-63-A reduced EGFP expression to 75.6%±2.6%, 44.1%±0.05% and 23.7%±0.62% when cells were exposed to 10, 40 and 150 nM, respectively. K-63-A-del-14 reduced GFP expression to 83.2%±4.0%, 51.4%±0.07% and 18.9%±13% when cells were exposed to 10, 40 and 150 nM, respectively.

Conclusions:

K-63-A is a potent moiety for delivery of macromolecular siRNA across phospholipid membranes. Installment of additional K-63-A moiety manifests cooperativity and synergy in the trans-membrane delivery process.

The invention claimed is:

1. A Conjugate, having the structure as set forth in Formula (I):

Formula (I)

including pharmaceutically-acceptable salts, hydrates, solvates and metal chelates of the compound represented by the structure as set forth in Formula (I), and solvates and hydrates of the salts, wherein:

D is the drug to be delivered across biological membranes, selected from a group consisting of a small-molecule drug, a peptide, a protein, and a native or modified, single-stranded or double-stranded DNA or RNA, siRNA or ASO;

y, z and w are each an integer, independently selected from 0, 1, 2, 3, 4, 5 or 6, wherein whenever the integer is 0, it means that the respective E moiety is null; at least one of y, z or w is different from 0;

wherein at least one of E, E' or E" has the structure as set forth in Formulae (IV) or (IVa):

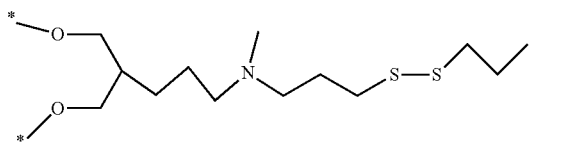

(Formula IV)

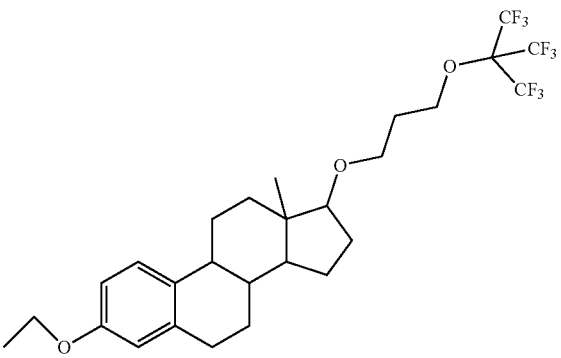

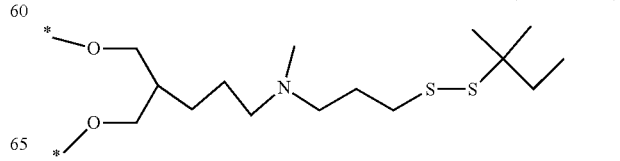

(Formula IVa)

-continued

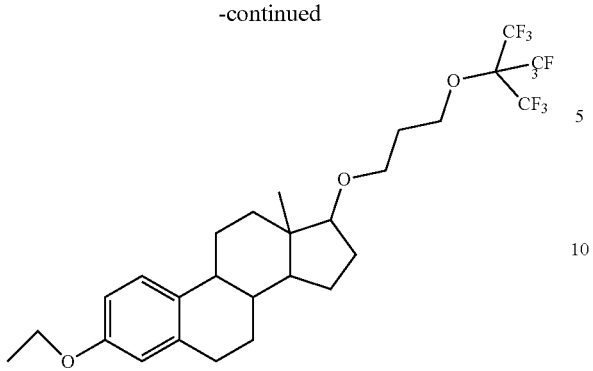

including pharmaceutically acceptable salts, hydrates, solvates and metal chelates of the compound represented by the structure as set forth in Formulae (IV) and (IVa), and solvates and hydrates of the salts.

2. A Conjugate, having the structure as set forth in Formula (I):

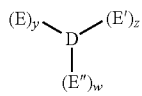

Formula (I)

including pharmaceutically-acceptable salts, hydrates, solvates and metal chelates of the compound represented by the structure as set forth in Formula (I), and solvates and hydrates of the salts, wherein:

D is the drug to be delivered across biological membranes, selected from a group consisting of a small-molecule drug, a peptide, a protein, and a native or modified, single-stranded or double-stranded DNA or RNA, siRNA or ASO;

y, z and w are each an integer, independently selected from 0, 1, 2, 3, 4, 5 or 6, wherein whenever the integer is 0, it means that the respective E moiety is null; at least one of y, z or w is different from 0;

wherein at least one of E, E' or E" has the structure as set forth in Formulae (V) or (Va):

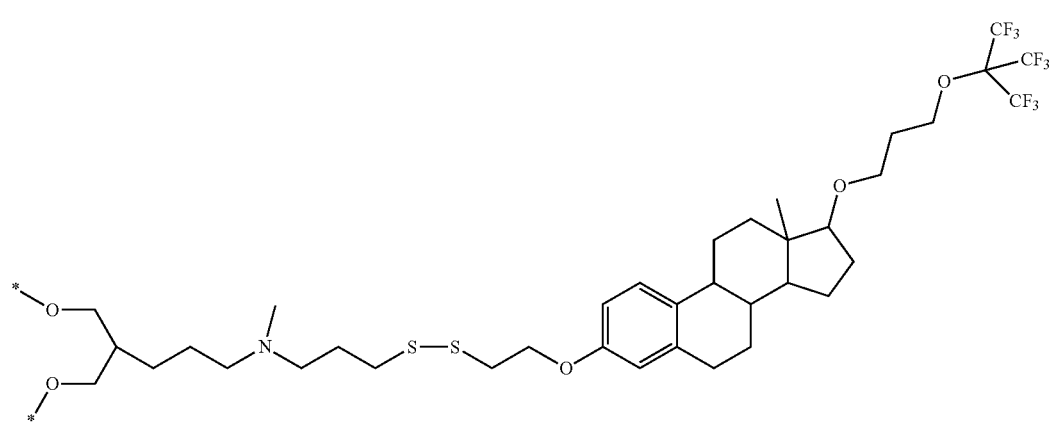

(Formula V)

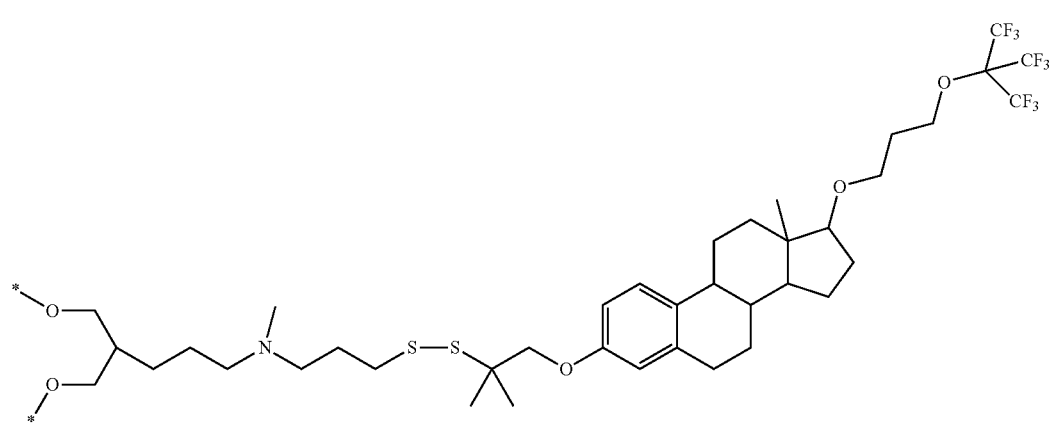

(Formula Va)

including pharmaceutically acceptable salts, hydrates, solvates and metal chelates of the compound represented by the structure as set forth in Formulae (V) or (Va), and solvates and hydrates of the salts.

3. A Conjugate according to claim 1 or 2, wherein the drug is a macromolecule drug, selected from the group consisting of siRNA, ASO and a therapeutic protein.

4. A pharmaceutical composition, comprising a Conjugate according to claim 1 or 2, and a pharmaceutically-acceptable salt or carrier.

5. A method for delivery of a drug into biological cells, wherein said cells are in culture, or in a living animal or a human subject; the method comprising contacting the cells with a Conjugate according claim 1 or 2.

6. A Conjugate according to claim 1 or 2, comprising a siRNA duplex, linked at each of its 5' ends to an E, E' or E" moiety, according to any of Formulae (IV), (IVa), (V), (Va).

7. A Conjugate according to claim 1 or 2, comprising a siRNA duplex, linked at each of its 5' ends, and also at an internal position within the siRNA duplex, to an E, E' or E" moiety, according to any of Formulae (IV), (IVa), (V), (Va).

8. A method for induction of strain and focal structural perturbations in the external leaflet of a phospholipid membrane of liposomes or biological cells, in vitro or in vivo; said method comprising interacting a Conjugate according to claim 1 or 2 with the phospholipid membrane, wherein the Conjugate comprises siRNA duplex, linked at each of its ends, and optionally also at an internal position within the siRNA duplex, to E, E' or E" moieties, each having the structure according to any Formulae (IV), (IVa), (V), (Va).

\* \* \* \* \*